(12) United States Patent
Murray et al.

(10) Patent No.: US 7,416,887 B2
(45) Date of Patent: Aug. 26, 2008

(54) METHODS FOR USE OF MPL LIGANDS WITH PRIMITIVE HUMAN STEM CELLS

(75) Inventors: Lesley J Murray, San Jose, CA (US); Judy C Young, San Carlos, CA (US)

(73) Assignee: Novartis AG, Cambridge, MA (US)

( * ) Notice: Subject to any disclaimer, the term of this patent is extended or adjusted under 35 U.S.C. 154(b) by 357 days.

(21) Appl. No.: 11/173,431

(22) Filed: Jul. 1, 2005

(65) Prior Publication Data
US 2006/0024275 A1  Feb. 2, 2006

Related U.S. Application Data

(60) Continuation of application No. 10/052,879, filed on Oct. 22, 2001, now Pat. No. 6,916,470, which is a continuation of application No. 09/328,188, filed on Jun. 8, 1999, now Pat. No. 6,326,205, which is a division of application No. 08/550,167, filed on Oct. 30, 1995, now Pat. No. 6,062,052.

(51) Int. Cl.
*C12N 15/85* (2006.01)
*C12N 5/08* (2006.01)
*C12N 5/02* (2006.01)

(52) U.S. Cl. .................. 435/325; 435/366; 435/384; 435/395

(58) Field of Classification Search .................. 435/325, 435/366, 384, 395
See application file for complete search history.

(56) References Cited

U.S. PATENT DOCUMENTS

| 4,714,680 A | 12/1987 | Civin |
| 5,061,620 A | 10/1991 | Tsukomoto et al. |
| 5,147,784 A | 9/1992 | Peault |
| 5,728,581 A | 3/1998 | Schwartz et al. |
| 5,989,537 A | 11/1999 | Holly et al. |

FOREIGN PATENT DOCUMENTS

| WO | WO 92/11355 | 7/1992 |
| WO | WO 95/03693 | 2/1995 |
| WO | WO 95/21626 | 8/1995 |
| WO | WO 96/40876 | 12/1996 |

OTHER PUBLICATIONS

Srivastava et al., Thrombopoietin enhances generation of CD34+ cells from human embryonic stem cells, 2007, Stem Cells, vol. 25, pp. 1456-1461.*
Abkowwitz et al., (1990) *Proc. Natl. Acad. Sci. USA* 87:9062-9066.
Bartley; et al., "Identification and cloning of a megakaryotic growth and development factor that is a ligand for the cytokine receptor mpl" *Cell*, (1994) vol. 77:1117-1124.
Baum, C. M.., et al., "Isolation of a Candidate Human Hematopoietic Stem-Cell Population," *Proc. Natl. Acad. Sci.* USA (Apr. 1992) vol. 89:2804-2808.
Berenson, R. J. et al., "Engraftment After Infusion of CD34+ Marrow Cells In Patients with Breast Cancer or Neuroblastoma," *Blood*, (Apr. 15, 1991) vol. 77, No.(8):1717-1722.
Bregni et al., "Human Peripheral Blood Hematopoietic Progenitors Are Optimal Targets Of Retroviral-Mediated Gene Transfer."(1992) *Blood* 80:1418-1422.
Breems, et al.,"Frequency analysis of human primitive haematopoietic stem cell . . . using a cobblestone area forming cell assay" (1994) *Leukemia* 8:1095.
Brenner, (1993)"Gene transfer into human hematopoietic progenitor cells: A review of current clinical protocols" *J. Hematother* 2:7-17.
Briddell et al., (1989)"Characterization of the human burst-forming unit-megakaryocyte" *Blood* 74:145.
Briddell et al., (1992) "Further phenotypic characterization and isolation of human hematopoietic progenitor cells using a monoclonal antibody to the c-kit receptor". *Blood* 79:3159-3167.
Broudy, et al. Thrombopoietin (c-mpl ligand) acts synergistically with erythropoietin, stem cell factor, and interleukin-11 to enhance murine megakaryocyte colony growth and increases megakaryocyte ploidy in vitro.(1995) *Blood* 85:1719-1726.
Bruno et al., "Interacting cytokines regulate in vitro human megakaryocytopoiesis" (1989) *Blood* 73:671.
Bruno, et al., Signal transduction by the receptors for thrombopoietin (c-mpL) and interleukin-3 in hematopoietic and nonhematopoietic cells (1995) *Blood* (Apr. 15, 1991) vol. 86, No. (10): Abstract 1449.
Capel, (1990) Long- and short-lived murine hematopoietic stem cell clones individually identified with retroviral integration markers, *Blood* 75:2267.
Chaudhary & Roninson (1991) "Expression and Activity of P-plycoprotein, a Multidrug efflux pump, In Human Hematopoietic Stem Cells", Cell:66:85.
Chen et al., (1993) Blood 82 (Suppl. 1):180a.
Chen, B. P., et al., "Engraftment of Human Hematopoietic Precursor Cells with Secondary Transfer Potential in SCID-hu Mice," *Blood* (Oct. 15, 1994) vol. 84, No. (8):2497-2505.
Choi, E. S. et al., "Platelets Generated in Vitro from Platelet-Displaying Human Megakaryocytes are Functional," *Blood* (Jan. 15, 1995) vol. 85, No.(2):402-413.
Chu et al., "Electroporation for the efficient transfection of mammalian cells with DNA", (1987) *Nucleic Acids Res.* 15:1311.
Craig,. et al., "Expression of Thy-1 on Human Hematopoietic Progenitor Cells," *J. Exp. Med.* (May 1993) vol. 177:1331-1342.

(Continued)

*Primary Examiner*—Peter Paras, Jr.
*Assistant Examiner*—David A. Montanari
(74) *Attorney, Agent, or Firm*—Dorsey & Whitney LLP

(57) ABSTRACT

Myeloproliferative leukemia receptor (mpl) ligands, such as thrombopoietin, act on a primitive subpopulation of human stem cells having the characteristics of self-renewal and ability to give rise to all hematopoietic cell lineages. Thrombopoietin supports both megakaryocytic differentiation and primitive progenitor cell expansion of $CD34^+$ and $CD34^+$ sub-populations ($CD34^+Lin^-$, $CD34^+Thy-1^+Lin^-$, and $CD34^+Lin^- Rh123^{-lo}$). Thrombopoietin also stimulated quiescent human stem cells to begin cycling. Thus, mpl ligands are useful for expanding primitive stem cells for restoration of hematopoietic capabilities and for providing modified human stem cells for gene therapy applications.

22 Claims, 9 Drawing Sheets

OTHER PUBLICATIONS

Debili, N. et al., "The MPL Receptor is Expressed in the Megakaryocytic Lineage from Late Progenitors to Platelets," *Blood* (Jan. 15, 1995) vol. 85,No. (2):391401.

deSauvage, F. et al., "Stimulation of Megakaryocytopoiesis and Thrombopoiesis by the c-Mpl Ligand," *Nature* (Jun. 16, 1994) vol. 369:533-538.

deSauvage, F. et al., Physiological regulation of early and late stages of megakaryocytopoiesis by thrombopoietin *Journal of Experimental Medicine* (Feb. 1, 1996) vol. 183:651-656.

DiGiusto et al., (1994) "Human fetal bone marrow early progenitors for T, B, . . . in the population expressing high levels of CD34" Blood 84:421.

Eck & Wilson, "Gene-Based Therapy" in Goodman and Gilman's *The Pharmacological Basis of Therapeutics*, McGraw-Hill: new York, Ninth Edition, pp. 77-101, 1996.

Fleming et al., "Functional Heterogeneity is Associated with the Cell Cycle Status of Murine Hematopoietic Stem Cells" (1993) *J. Cell Biol.* 122:897-902.

Galy et al. Generation of T cells from cytokine-mobilized peripheral blood and adult bone marrow CD34+ cell (1994) 84:104-110.

Guerney, A. L. et al., "Thrombocytopenia in c-Mpl Deficient Mice", *Science*, (Sep. 1994) vol. 265:1445-1447.

Gilboa (1988) "Retroviral gene transfer: Applications to human therapy" *Adv. Exp. Med. Biol.* 241:29.

Haapala et al. (1985) "Isolation from cats of an endogenous type C virus with a novel envelope glycoprotein", *J. Virol.* 53:827.

Harrison et al., (1993) "Number and continuous proliferative pattern of transplanted primitive immunohematopoietic stem cell", *Exp. Hematol.* 21:206-219.

Harrison & Zhong (1992) "The same exhaustible precursor produces both myeloid and lymphoid cells as early as 3-4 weeks after marrow transplantation," *Proc. Natl. Acad. Sci. USA* 89:10134-10138.

Jurecic et al., (1993) Enrichment and functional characterization of Sca-1+WGA+, Lin-WGA+, Lin- Sca-1+, and Lin-Sca-1+WGA+ bone marrow cells from mice with an Ly-6a haplo Blood 82:2673-2683.

Jones et al., (1990) "Separation of pluripotent haematopoietic stem cells form spleen colony-forming cells" *Nature* 347:188-189.

Jordan et al., (1990) "Cellular and developmental properties of fetal hematopoietic stem cells", *Cell* 61:953.

Jones et al., "Two phases of engraftment established by serial bone marrow transplantation in mice," (1989) *Blood* 73:397-401.

Jorgensen, et al., (1994) *Blood* vol. 84, No. (10):Abstract 1301.

Kaushansky, et al., (1995) "Thrombopoietin expands erythroid progenitors, increases red cell production and enhances erythroid recovery after myleosupressive therapy", *J. Clin. Invest.* vol. 96:1683-1687.

Kaushansky, et al., "Promotion of megakaryocyte progenitor expansion and differentiation by the c-Mpl ligand throm- bopoietin," *Nature* vol. 369:568-571.

Kaushansky, (1994) "The mpl Ligand: Molecular and Cel -lular Biology of the Critical Regulator ol Megakaryocyte Development," et al., *Stem Cells* 12:91-97.

Kuter et al., (1994) The purification of megapoietin: a physiological regulator of megakaryocyte growth and platelet production. *Proc. Natl. Acad. Sci. USA* 91:11104-11108.

Kuter & Rosenberg (1994) The Purification of Megapoietin: A Physiological Regulator of Megakaryocyte Growth and Platelet Production *Blood* 84:1464.

Kyoizumi et al., (1992) *Blood* 79:1704.

Lansdorp et al., (1990) "Selective expression of CD45 isoforms on functional from human bone marrow" *J. Exp. Med.* 172:363-366.

Lansdorp et al., (1993) "Long-term erythropoiesis from constant numbers of CD34+ cells in progenitor cells" *J. Exp. Med.* 177:1331.

Li & Johnson (1992) "Rhodamine 123 reveals heterogeneity within murine Lin~, Sca-l+ hemopoietic stem cells", *J. Exp. Med.* 175:1443-1447.

Lok, et al., (1994) *Nature* 269:565.

Lok & Foster (Nov. 1994) "The structure, biology and potential therapeutic applications of recombinant thrombopoietin" *Stem Cells* vol. 12:586-598.

Luskey et al., (1990) "Gene transfer into murine hematopoietic stem cells and bone marrow stromal cells" *Ann. N. Y. Acad. Sci.* 612:398.

Lu et al., "High Efficiency Retroviral Mediated Gene Transduction into Single Isolated Immature and Replatable CD34$^{3+}$ Hematopoietic Stem/Progenitor Cells from Human Umbilical Cord Blood", *Journal of Experimental Medicine*, vol. 178,pp. 2089-2096, Dec. 1993.

Markowitz et al., (1988) A Safe Packaging Line for Gene Transfer: Separating Viral Genes on Two Different Plasmids *J. Virol.* 62:1120.

Marsh et al., (1992) *Leukemia* 6:929.

Metcalf (1977)Hemopoietic Colonies. In vitro Cloning of Normal and Leukemic Cells, In: *Recent Results in Cancer Research 61*, Springer-Verlag, Berlin, pp. 1-227.

Methia et al., Oligodeoxynucleotides antisense to the proto-oncogene c-mpl specifically inhibit in vitro megakaryocytopoiesis (1993) *Blood* 82:1395-1401.

Miller & Buttimore Redesign of Retrovirus packaging cell lines to avoid recombination leading to helper virus cell production, (1986) *Mol. Cell Biol.* 6:2895.

Miller & Rosman (1989) "Improved retroviral vectors for gene transfer and expression", *Biotechniques* 7:980.

Miller, (1992) "Human gene therapy comes of age" *Nature* 357:455-460.

Mitani et al., *Human Gene Therapy*, vol. 5, pp. 941-948, Aug. 1994.

Murray, L. et al., "Analysis of Human Hematopoietic Stem Cell Populations", *Blood Cells* (1994) vol. 20:364-370.

Murray, L. et al., "Enrichment of Human Hematopoietic Stem Cell Activity in the CD34+Thy-1+lin Subpopulation from Mobilized Peripheral," *Blood* (Jan. 15, 1995) vol. 85, No. (2):368-378.

Neben et al., "Quantitation of murine hematopoietic stem cells in vitro" (1993) *Exp. Hematol.* 21:438.

Nienhuis et al., "Gene Transfer into Hematopoietic Stem Cells", *Cancer* 67:2700-2704 (1991).

Ploemacher et al., "Use of limiting dilution type long-term bone marrow cultures in frequencey analysis of marrow-repopulating and spleen colony forming hemopoietic cells in the mouse," (1991) *Blood* 78:2527.

Ploemacher & Brons (1994) *Exp. Hematol.* 17:263-266.

Reading, et al., (1994) Proceeding of ISEH Meeting 1994, Abstract, *Exp. Hematol.* vol. 22:786.

Schmidt-Wolf et al., *Journal of Hematotherapy*, vol. 4, pp. 551-561, 1995.

Skoda et al., "Murine c-mpl: a member of the hematopoietic growth factor receptor superfamily that transduces a proliferative signal" *EMBO J.* 12:2645-2653 (1993).

Smith)"Retroviral vector-mediated gene transfer into hematopoietic cells: Prospects and issues" *J. Hemtatother* 1:155-166, (1992.

Souyri et al., "A Putative Truncated Cytokine Receptor Gene Transduced by the Myeloproliferative Leukemia Virus Immortalizes Hematopoietic Progenitors", (1990) Cell 63:1137-1147.

Spangrude, G. J. et al., "Purification and Characterization of Mouse Multipotent Hematopoietic Stem Cells," *Science* (Jul. 1988) vol. 241:58-62.

Spangrude, G. J. et al., "Enrichment of murine haemopoietic stem cells: divering roads" (1989) *Immunol. Today* 10:344-350.

Spangrude, G. J. et al., "Resting and Activated Subsets of Mouse Hematopoietic Stem Cells," *Proc. Natl. Acad. Sci. USA* (Oct. 1990) 7433-7437.

Spangrude & Scollay (1990) *Exp. Hematol.* 18:9920-926.

Srour et al Simultanoeus Use of Rhodamine 123, Phycoerythrin, Texas Red, and Allophycocyanin for the Isolation of Human Hematopoietic Progenitor cells. (1991) *Cytometry* 12:179.

Srour et al., (1992)"Animal models for human hematopoiésis" *J. Hematother.* 1:143-153.

Sutherland et al.,"Functional characterization of individual human hematopoietic stem cells cultured at limiting dilution on supportive marrow stromal layers" *Proc. Natl. Acad. Sci. USA* 87:3584-3588 (1990).

Sutherland, D. R., et al., "Differential Sensitivity of cd34 Epitopes to Cleavage by *Pastereulia haemolytica* Glycoprotease :Implications for Purification of cd34-positive progenitor cells", *Exp. Hematol.* (1992) vol. 20:590-599.

Szilvassay et al., (1989) *Blood* 74:930-939.

Szilvassay & Cory (1993) *Blood* 81:2310-2320.

Uchida & Weissman "Searching for hematopoietic stem cells: evidence that Thy-1.1lo Lin- Sca-1+ cells are the only stem cells in C57BL/Ka-Thy-1.1 bone marrow" *J. Exp. Med.* 175:175-184 (1992).

Uchida et al. "Rapid and Sustained Hematopoietic Recovery in Lethally Irradiated Mice Transplanted with Purified Thy-1.1lo Lin-Sca-1&plus Hematopoietic Stem Cells", *Blood* 83:3758-3779. (1994).

Udomsadki et al., (1991) *Exp. Hematol.* 19:338.

Verfaille et al., Purified Primitive Human Hematopoietic Progenitor Cells with Long-Term In Vitro Repopulating Capacity Adhere Selectively to Irradiated Bone Marrow Stroma *J. Exp. Med.* 172:509-520 (1990).

Vigon et al., Expression of the c-mpl Proto-oncogene in Human Hematologic Malignancies, *Proc Natl. Acad. Sci. USA* 89:5640-5644 (1992).

Visser & Van Bekkum "Purification of pluripotent hemopoietic stem cells: past and present" *Exp. Hematol.* 18:248-256. (1990).

Wendling, et al, "C-Mpl ligand is a humoral regulator of megakaryocytopoiesis". *Nature* 369:571.

Wendling, et al., "Factor-independent erythropoietic progenitor cells in leukemia induced by the myeloproliferative leukemia virus," (1989) *Blood* 73:1161-1167.

Whitlock et al., "Bone marrow stromal cell lines with lymphopoietic activity express high levels of pre-B neoplasia associated molecule" *Cell* 48:1009-1021 (1987).

Wolf et al., "In Vivo and In Vitro Characterization of Long-Term Repopulating Primitive Hematopoietic Cells Isolated by Sequential Hoechst 33342-Rhodamine 123 FACS Selection," *Exp. Hematol.* 21:614-622., (1993).

Young, et al., *Blood*, "Thrombopoietin stimulates megakaryocytopoiesis, myelopoiesis, and expansion of CD34+ progenitor cells from single CD34+Thy-1+Lin- primitive progenitor cells" (Sep. 1, 1996) vol. 88:1619-1631.

Zanjani et al., (1992) *J. Clin. Invest* 89:1179.

Ziegler, F. C., et al., "In vitro Megakaryocytopoeitic and Throbopoietic Activity of c-mpl Ligand (TPO) on Purified Murine Hematopoietic Cells," *Blood* (Dec. 1994) vol. 84, No. (12):4045-4052.

\* cited by examiner

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA
        (B) MAP POSITION: Positions 30, 31, 33

(ix) FEATURE:
        (A) NAME/KEY: Inosine (xi) SEQUENCE DESCRIPTION: SEQ ID NO: 1:

GCTATTGCGG CCGCGAATTC GGARGAYYTN NNNTGYTTYT GG                          42

(2) INFORMATION FOR SEQ ID NO: 2:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA
        (B) MAP POSITION: Positions 24, 33, 34, 35

(ix) FEATURE:
        (A) NAME/KEY: Inosine (xi) SEQUENCE DESCRIPTION: SEQ ID NO: 2:

GCTATTCTCG AGATCGATSW CCANTCRCTC CANNNNCC                                          38

(2) INFORMATION FOR SEQ ID NO: 3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA
        (B) MAP POSITION: Positions 24, 26, 33, 34, 35

(ix) FEATURE:
        (A) NAME/KEY: Inosine (xi) SEQUENCE DESCRIPTION: SEQ ID NO: 3:

GCTATTCTCG AGATCGATSW CCANNNRCTC CANNNNCC                                          38

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

CGCTGCACCT CTGGGTGAAG                                                              20

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

AGCAGGGCAG CAGGTTTCTG T                                                            21

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

GCTGCGCAGC TGCAGCCAGT A                                                            21

METHODS FOR USE OF MPL LIGANDS WITH PRIMITIVE HUMAN STEM CELLS

CROSS-REFERENCE TO RELATED APPLICATIONS

This is a continuation of application Ser. No. 10/052,879, filed Oct. 22, 2001 now U.S. Pat. No. 6,916,470 which is a continuation of application Ser. No. 09/328,188, filed Jun. 8, 1999, now U.S. Pat. No. 6,326,205, which is a divisional of application Ser. No. 08/550,167, filed Oct. 30, 1995, U.S. Pat. No. 6,062,052, the specifications of which are hereby incorporated by reference.

FIELD OF THE INVENTION

This invention relates to myeloproliferative receptors (mpl), specifically, the use of mpl ligands to expand primitive human stem cell subpopulations with minimal differentiation.

BACKGROUND OF THE INVENTION

Thrombopoietin (TPO) is a recently isolated ligand of mpl (Bartley et al. (1994) Cell 77:1117; Kaushansky et al. (1994) Nature 369:568; Lok et al. (1994) Nature 269:565; Kuter et al. (1994) Proc. Natl. Acad. Sci. USA 91:11104-11108; Kuter & Rosenberg (1994) Blood 84:1464; Wendling et al. (1994) Nature 369:571), first identified as the proto-oncogene transduced by the murine myeloproliferative leukemia (MPL) virus (Wendling et al. (1989) Blood 73:1161-1167; Souyri et al. (1990) Cell 63:1137-1147; Vigon. et al. (1992) Proc. Natl. Acad. Sci. USA 89:5640-5644; Skoda et al. (1993) EMBO J. 12:2645-2653; Methia et al. (1993) Blood 82:1395-1401). TPO has been shown to independently stimulate megakaryocyte (MK) progenitor division and MK maturation in vivo and in vitro (Bartley et al. (1994). supra; Kuter et al. 1994) supra; Kuter & Rosenberg (1994) supra; Wendling et al. (1994) supra; de Sauvage et a. (1994) Nature 369:533; Broudy et al. (1995) Blood 85:1719-1726; Lok & Foster (1994) Stem Cells 12:586-598; Zeigler et al. (1994) Blood 84:4045). In vivo administration of TPO to thrombocytopenic rodents was found to significantly boost the platelet count as well as increase the number and ploidy of maturing MKs in the bone marrow (Lok et al. (1994) supra; Lok et al. (1994) supra; Wendling et al. (1994) supra; de Sauvage et al. (1994) supra). Absence of a c-mpl (TPO receptor) gene in mice was reported to result in thrombocytopenia (Guerney et al. (1994) Science 265:1445). More recently, it has been demonstrated that MKs can be primed to produce functional platelets in culture after exposure to TPO (Choi et al. (1995) Blood 85:402).

Hematopoietic stem cells are rare cells that have been identified in fetal bone marrow, umbilical cord blood, adult bone marrow, and peripheral blood, which are capable of differentiating into each of the myeloerythroid (red blood cells, granulocytes, monocytes), megakaryocyte (platelets) and lymphoid (T-cells, B-cells, and natural killer cells) lineages. In addition, these cells are long-lived, and are capable of producing additional stem cells, a process termed self-renewal. Stem cells initially undergo commitment to lineage restricted progenitor cells, which can be assayed by their ability to form colonies in semisolid media. Progenitor cells are restricted in their ability to undergo multi-lineage differentiation and have lost their ability to self-renew. Progenitor cells eventually differentiate and mature into each of the functional elements of the blood. This maturation process is thought to be modulated by a complex network of regulatory factors including erythropoietin (EPO), granulocyte colony stimulating factor (G-CSF), granulocyte-macrophage colony stimulating factor (GM-CSF), thrombopoietin (TPO), steel factor (Stl), Flk-2 ligand and interleukins (IL) 1-15.

Recently, in vitro assays have been developed to identify human hematopoietic stem cells having self-renewal and multi-lineage differentiative capacity. One assay is the cobblestone area-forming cell (CAFC) assay, based on. freshly isolated stromal cells or established stromal cell lines. In the mouse system, late-appearing cobblestone area formation on fresh marrow-derived stroma (Ploemacher et al. (1991) Blood 78:2527) or on a cloned stromal cell line (Neben et al. (1993) Exp. Hematol. 21:438) has been shown to correlate with in vivo hematopoietic repopulating ability. Correlation of CAFC and long term culture-initiating cell (LTCIC) frequencies using the mouse stromal cell line Sys1 has been demonstrated (Reading et al. (1994) Exp. Hematol. 22:406). In addition, the in vivo severe combined immunodeficiency (SCID)-hu bone assay has been used to measure long term engraftment of candidate stem cell populations (Kyoizumi et al. (1992) Blood 79:1704; Baum et al. (1992) Proc. Natl. Acad. Sci. USA 89:2804.; Chen et al. (1993) Blood 82 (Suppl. 1):180a). Both the in vitro CAFC assay and the SCID-hu bone model permit analysis of B-cell and myeloid cell generation from candidate pluripotent hematopoietic stem cells (PHSC).

It is becoming increasingly apparent that distinct subpopulations of stem cells may be responsible for different phases of engraftment post transplantation. As early as 1964, differences in the ability of murine spleen colony forming units (CFU-S) to generate secondary CFU-S were defined (Ploemacher & Brons (1994) Exp. Hematol. 17:263-266). Although evidence now indicates that most CFU-S are not involved in repopulating lethally irradiated hosts (Jones et al. (1990) Nature 347:188-189; Jones et al. (1989) Blood 73:397-401), heterogeneity in transplantation potential appears to exist even within subpopulations of radioprotective cells. This has been demonstrated with serial bone marrow transplantations. The long-term repopulating ability of the grafts are lost with serial transfers, while a cell population survives which contributes to short-term reconstitution (Jones et al. (1989) supra). Further support for the concept that both short-term and long-term reconstituting stem cell populations exist have been derived from studies in which isoenzyme analysis and retroviral gene marking of hematopoietic cells have been utilized to track the fate of stem cells. A mathematical analysis of correlations and variances of donor reconstitution with isoenzyme variants in lethally irradiated mice indicates that a large number of multi-lineage clones are active immediately after reconstitution but rapidly decline, with the majority being inactive 12 weeks post-transplantation (Harrison & Zhong (1992) Proc. Natl. Acad. Sci. USA 89:10134-10138; Harrison et al. (1993) Exp. Hematol. 21:206-219). These observations indicate the existence of a population of cells with multi-lineage short-term engrafting potential in donor murine bone marrow. Similar observations have been made in a large animal transplantation model, where isoenzyme differences have indicated the contribution of multiple clones to short-term engraftment followed by sustained contributions by relatively few stem cell clones (Abkowwitz et al. (1990) Proc. Natl. Acad. Sci. USA 87:9062-9066). These findings have been confirmed by an eloquent analysis of clonal development after transplantation with retrovirally marked stem cells (Jordan et al. (1990) Cell 61:953; Capel et al. (1990) Blood 75:2267).

Theoretically, subsets of cells with differing proliferative potentials may also differ with regards to physical characteristics, and therefore may be isolated and functionally defined. Bone marrow cells responsible for reconstitution following lethal irradiation can be isolated using centrifugation techniques exploiting cell size and density fractionation, or fluorescence-activated cell sorting (FACS) based on uptake of fluorescent vital dyes, lectin binding, or cell surface antigen expression (Sprangrude (1989) Immunol. Today 10:344-350; Visser & Van Bekkum (1990) Exp. Hematol. 18:248-256). FACS isolated murine cells that are responsible for engraftment lack lineage markers for B-cells, T-cells, myelomonocytes and erythrocytes and are termed lineage negative ($Lin^-$) (Spangrude et al. (1988) Science 241:58-62). The $Lin^-$ fraction of murine bone marrow can be further subdivided based on low levels of Thy-1 and expression of the Sca-1 antigen (Visser & Van Bekkum (1990) supra; Spangrude et al. (1988) supra; Szilvassay et al. (1989) Blood 74:930-939; Szilvassay & Cory (1993) Blood 81:2310-2320; Spangrude & Scollay (1990) Exp. Hematol. 18:9920-926; Jurecic et al. (1993) Blood 82:2673-2683). Murine cells that are Thy-1.$1^{lo}Lin^-$Sca-$1^+$ are 1000-fold enriched in radioprotective ability, and contain all of the radioprotective cells found in the bone marrow of syngeneic C57BL/thy-1.1 mice (Uchida & Weissman (1992) J. Exp. Med. 175:175-184). As few as 100 cells that are Thy-1.$1^{lo}Lin^-$Sca-$1^+$ can radioprotect at least 95% of lethally irradiated recipients with long term donor derived reconstitution. At this cell dose, Thy-1.$1^{lo}Lin^-$ Sca-$1^+$ cells give rise to donor peripheral blood white blood cells by 10 days post transplant, and to platelets within 14 days of transplant (Uchida et al. (1994) Blood 83:3758-3779). These studies suggest this population contains cells with both short-term and long-term engrafting potential.

Thy-1.$1^{lo}Lin^-$Sca-$1^+$ cells can be further divided by heterogeneity of cell cycle status and uptake of a fluorescent dye, rhodamine 123 (Spangrude & Johnson (1990) Proc. Natl. Acad. Sci. USA 87:7433-7437; Li & Johnson (1992) J. Exp. Med. 175:1443-1447; Fleming et al. (1993) J. Cell Biol. 122:897-902; Wolf et al. (1993) Exp. Hematol. 21:614-622). Rhodamine 123 is a dye that identifies active mitochondria, and its efflux from the cell is handled by the multidrug resistance gene product, P-glycoprotein. Those cells that retain small quantities of rhodamine 123 are termed rhodamine dull (or low) and have been shown to possess marrow repopulating ability (MRA) (Li & Johnson (1992) supra).

The cells responsible for reconstituting hematopoiesis in humans receiving a bone marrow transplant reside in a subset of cells expressing the CD34 antigen ($CD34^+$) (Berenson et al. (1991) Blood 77:1717-1722). This fraction of cells can be further subdivided based on multiple antigen characteristics (Lansdorp et al. (1990) J. Exp. Med. 172:363-366; Verfaille et al. (1990) J. Exp. Med. 172:509-520; Briddell et al. (1992) Blood 79:3159-3167) including the lack of lineage specific markers ($Lin^-$) and expression of the Thy antigen ($Thy-1^+$) (Baum et al. (1992) Proc. Natl. Acad. Sci. USA 89:2804-2808; Craig et al. (1993) J. Exp. Med. 177:1331-1342; Murray et al. (1990) Blood Cells 20:364-370; Murray et al. (1995) Blood 85:468). In. vivo assays using adult bone marrow and mobilized peripheral blood cells that are $CD34^+Thy-1^+Lin^-$ have shown that this population contains cells capable of contributing to all hematopoietic lineages (Chen et al. (1994) Blood 84:2497-2505; Galy et al. (1994) 84:104-110).

Mpl expression has been detected by polymerase chain reaction (PCR) in human hematopoietic cells throughout the MK lineage, as well as in primitive $CD34^+CD38^{lo/-}$ cells (Debili et al. (1995) Blood 85:391-401). However, little is known about the actions of TPO on primitive cells prior to commitment to the MK lineage. One report has shown that primitive mouse HSC of the phenotype Sca-$1^+AA4^+$ express mpl, and exposure of these cells to TPO in vitro resulted in MK differentiation (Zeigler et al. (1994) supra).

SUMMARY OF THE INVENTION

The present invention is based in part on the discovery that human stem cells respond to ligands which bind and activate the myeloproliferative leukemia receptor (mpl) by expansion of primitive non-megakaryocytic blast cells, as well as expansion of megakaryocytic (MK) progenitor cells, commitment to the MK lineage, and MK maturation. These discoveries provide the basis for new uses, including therapeutic uses of mpl ligands for in vitro and in vivo stem cell activation and expansion.

The subset of primitive human stem cells described and disclosed herein to express mpl and respond to a mpl ligand, thrombopoietin (TPO), have the ability to reconstitute hematopoiesis in humans receiving a bone marrow transplant. The stem cells useful in this invention are characterized by their ability to undergo substantial self-renewal and to proliferate and differentiate into cells of all the hematopoietic lineages. These cells may be identified by cell surface markers such as the CD34 antigen ($CD34^+$). More preferably, the stem cells useful in the invention are enriched for the ability to undergo substantial self-renewal and to proliferate and differentiate into cells of all the hematopoietic lineages. A more enriched subpopulation of cells may be identified by the lack of lineage specific markers ($Lin^-$), and/or expression of the Thy-1 antigen ($Thy-1^+$) (Baum et al. (1992) supra; Craig et al. (1993) supra). e.g., $CD34^+Lin^-$ or $CD34^+Thy-1^+Lin^-$. These cells are highly enriched in pluripotent cells with long-term and short-term repopulating potential. Alternatively, an enriched subpopulation of cells with the desired characteristics may be identified by the cell markers $CD34^+Lin^-Rho^{lo}$ or $CD34^+Thy-1^+Lin^-Rho^{lo}$. The subpopulations of stem cells useful in this invention may also be identified by their light scattering characteristics, e.g., low side scatter and low-to-medium forward scatter profiles by FACS analysis, and/or by phenotype, e.g., having a size between mature lymphoid cells and mature granulocytes.

The present invention features a method for promoting the survival of long-term repopulating human stem cells by culturing such cells in the presence of a mpl ligand. The mpl ligand of the invention is characterized by the ability to bind mpl such that mpl-mediated biological activity is initiated. In a preferred embodiment, the mpl ligand is TPO, more preferably, human TPO, and still more preferably, recombinant human TPO. Stem cells cultured in the presence of a mpl ligand (e.g., TPO) retain the ability to undergo substantial self-renewal and to proliferate and differentiate into cells of all the hematopoietic lineages, i.e., are pluripotent hematopoietic stem cells.

The invention features the use of a mpl ligand on a primitive subpopulation of human stem cells to expand the population of stem cells with minimal concomitant induction of differentiation. The expanded cell population is characterized by the ability to generate cells capable of substantial self-renewal and proliferation and differentiation into cells of all of the hematopoietic lineages.

The invention features a therapeutic method for restoring hematopoietic capability to a human subject. Stem cells are purified from cells removed from a subject, expanded by in vitro exposure to a mpl ligand, and returned to the subject, resulting in restoration of hematopoietic capability to the subject. In addition to expansion in the presence of the mpl ligand thrombopoietin, in vitro expansion of stem cells can be conducted in the presence of additional cytokines, including for example interleukin-3 (IL-3), leukemia inhibitory factor (LIF), and steel factor (Stl) (also known as c-kit ligand (KL) or stem cell factor (SCF)), interleukin 6 (IL-6), fetal liver tyrosine kinase ⅔ (Flk2/Flt3), macrophage inhibitory protein-1α (MIP-1α), granulocyte-macrophage colony stimulating factor (GM-CSF), granulocyte colony stimulating factor (G-CSF), IL-1, and IL-11.

The invention features a method for activating quiescent stem cells to divide by exposing such cells to a mpl ligand. This aspect of the invention has important clinical implications, including improved transduction of hematopoietic cells by a retroviral vector for use in gene therapy.

Accordingly, in a related aspect, quiescent stem cells are activated in the presence of a mpl ligand, and cultured with a retroviral vector containing a gene of interest. The actively dividing cells integrate the gene of interest, and express the foreign gene product. Such transformed stem cells are useful for gene therapy applications.

In the gene therapy aspect of the invention, hematopoietic cells are removed from a subject, transduced in vitro in the presence of a mpl ligand and a retroviral vector, and the modified cells returned to the subject. The modified stem cells and their progeny will express the desired gene product in vivo, thus providing sustained therapeutic benefit.

In addition to the advantages of stem cell expansion with minimal differentiation and stem cell activation, other advantages and features of the present invention will become apparent to those skilled in the art upon reading this disclosure.

BRIEF DESCRIPTION OF THE FIGURES

FIG. 2A, control; FIG. 2C, TPO; FIG. 2E, KL; FIG. 2G, IL-3; FIG. 2I, IL-3+TPO; FIG. 2K, KL+TPO. Day 6: FIG. 2B, control; FIG. 2D, TPO; FIG. 2F, KL; FIG. 2H, IL-3; FIG. 2J, IL-3+TPO; FIG. 2L, KL+TPO.

DETAILED DESCRIPTION

Figure 1A:
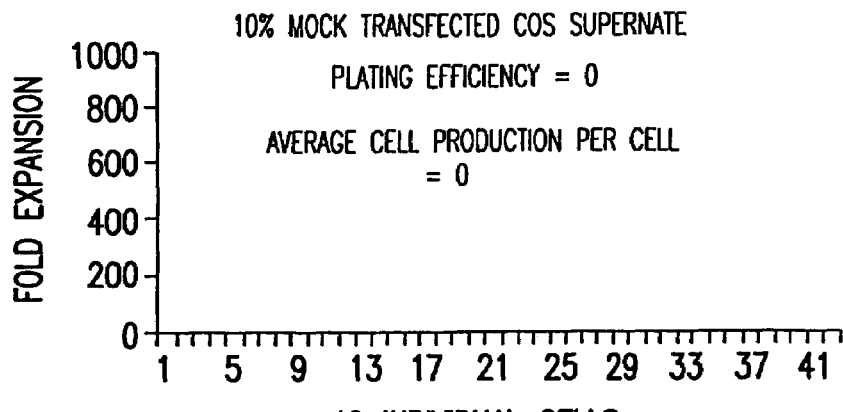
FIG. 1A is a graph showing the proliferative capacity of $CD34^+Thy-1^+Lin^-$ cells purified from adult bone marrow (ABM) and cultured individually in the presence of 10% supernatant from COS cells transfected with an empty expression vector (control). Each bar represents the maximum proliferation achieved by each cell plated over a four weeks culture period, as determined from each series of bi-weekly images.

Before the present invention and methods for using same are described, it is to be understood that this invention is not limited to the particular cell lines, mpl ligand, or methodology described. It is also to be understood that the terminology used herein is for the purpose of describing particular embodiments only and is not intended to be limiting since the scope of the present invention will be limited only by the appended claims.

It must be noted that as used in this specification and the appended claims, the singular forms "a", "an" and "the" include plural references unless the context clearly dictates otherwise. Thus, for example, reference to "a stem cell" includes a plurality of cells, including mixtures thereof, and reference to "a mpl ligand" include compounds able to bind mpl with sufficient specificity to elicit mpl-mediated biological activity.

Unless defined otherwise, all technical and scientific terms used herein have the same meaning as commonly understood by one of ordinary skill in the art to which this invention belongs. Although any methodology and materials similar or equivalent to those described herein can be used in the practice or testing of the present invention, the preferred methods and materials are now described. All publications mentioned herein are incorporated herein by reference for the purpose of disclosing and describing the particular materials and methodologies for which the reference was cited in connection with.

Definitions

By the term "mpl ligand" is meant a compound capable of binding to mpl such that one or more mpl-mediated biological actions are initiated. As herein disclosed, mpl-mediated biological activity includes (1) promotion of the survival of stem cells in culture, such that the cell maintains the capability of self-renewal and the ability to give rise to all hematopoietic cell lineages, (2) expansion of stem cell populations, such that the expanded cell population maintains the capability of self-renewal and the ability to give rise to all hematopoietic cell lineages, and (3) activation of a quiescent stem cell, such that the stem cell is activated to divide and the resulting cells maintain the capability of self-renewal and the ability to give rise to all hematopoietic cell lineages. The mpl ligand in the invention initiates at least one mpl-mediated activity, and preferably two or more mpl-mediated activities. Preferably, mpl ligand is thrombopoietin, and more preferably, human thrombopoietin, and still more preferably, recombinant human thrombopoietin. The term "mpl ligand" also includes antibodies to the mpl receptor capable of binding to mpl such that one or more of the above-described mpl-mediated biological actions are initiated. Such antibodies may consist essentially of pooled monoclonal antibodies with different epitopic specificities, or be distinct monoclonal antibodies. The term "mpl ligand" further includes mimetic molecules, e.g., small molecules able to bind mpl such that one or more of the above-described mpl-mediated biological actions are initiated. The methods and assays disclosed herein, combined with methods known to the art, are utilized to construct libraries of mimetic molecules, and to screen the libraries such that a TPO mimetic is identified having the requisite biological activity.

By the term "stem cell" is meant hematopoietic cells which are capable of self-regeneration when provided to a human subject in vivo, and may become lineage restricted progenitors, which further differentiate and expand into specific lineages. As used herein, "stem cells" refers to hematopoietic cells and not stem cells of other cell types. Further, unless indicated otherwise, "stem cells" refers to human hematopoietic stem cells.

The term "stem cell" or "pluripotent" stem cell are used interchangeably to mean a stem cell having (1) the ability to give rise to progeny in all defined hematopoietic is lineages, and (2) stem cells capable of fully reconstituting a seriously immunocompromised host in all blood cell types and their progeny, including the pluripotent hematopoietic stem cell, by self-renewal. A stem cell or pluripotent stem cell may be identified by expression of the cell surface marker $CD34^+$.

Stem cells constitute only a small percentage of the total number of hematopoietic cells. Hematopoietic cells are identifiable by the presence of a variety of cell surface "markers." Such markers may be either specific to a particular lineage or progenitor cell or be present on more than one cell type. CD34 is a marker found on stem cells and a significant number of more differentiated progenitor cells. U.S. Pat. No. 4,714,680 describes a population of cells expressing the CD34 marker.

As used herein, "stem cells" or "pluripotent stem cells" refers to a population of hematopoietic cells having all of the long-term engrafting potential in vivo. Animal models for long-term engrafting potential of candidate human hematopoietic stem cell populations include the SCID-hu bone model (Kyoizumi et al. (1992) Blood 79:1704; Murray et al. (1995) Blood 85:368-378) and the in utero sheep model (Zanjani et al. (1992) J. Clin. Invest. 89:1179). For a review of animal models of human hematopoiesis, see Srour et al. (1992) J. Hematother. 1:143-153 and the references cited therein. In vitro assays for stem cells include the long-term culture-initiating cell (LTCIC) assay, based on a limiting dilution analysis of the number of clonogenic cells produced in a stromal co-culture after 5-8 weeks (Sutherland et al. (1990) Proc. Natl. Acad. Sci. USA 87:3584-3588, and the cobblestone area forming cell (CAFC) assay, shown to correlate with the LTCIC assay and with long-term engrafting potential (Breems et al. (1994) Leukemia 8:1095).

For use in the present invention, a highly enriched stem cell population is preferred. An example of an enriched stem cell population is a population of cells selected by expression of the CD34 marker. In LTCIC assays, a population enriched in $CD34^+$ cells will typically have an LTCIC frequency in the range of 1/50 to 1/500, more usually in the range of 1/50 to 1/200. Preferably, the stem cell population will be more highly enriched for stem cells than that provided by a population selected on the basis of $CD34^+$ expression alone. By use of various techniques described more fully below, a highly enriched stem cell population may be obtained. A highly enriched stem cell population will typically have an LTCIC frequency in the range of 1/5 to 1/100, more usually in the range of 1/10 to 1/50. Preferably, it will have an LTCIC frequency of at least 1/50. Exemplary of a highly enriched stem cell population is a population having the $CD34^+Lin^-$ or $CD34^+Thy-1^+Lin^-$ phenotype as described in U.S. Pat. No. 5,061,620, incorporated herein by reference to disclose and describe such cells. A population of this phenotype will typically have an average LTCIC frequency of approximately 1/20 (Murray et al. (1995) supra; Lansdorp et al. (1993) J. Exp. Med. 177:1331). LTCIC frequencies are known to correlate with CAFC frequencies (Reading et al. (1994) supra).

Most preferably, the stem cell population will be enriched for the ability to efflux the mitochondrial dye rhodamine123 (Rh123). The ability to efflux Rh123 is a characteristic associated with the most primitive pluripotent human stem cell (Udomsakdi et al. (1991) Exp. Hematol. 19:338; Srour et al. (1991) Cytometry 12:179; Chaudhary & Roninson (1991) Cell 66:85). Thus, in the most preferred embodiment, the stem cell population is characterized by having the $CD34^+Lin^-Rh123^{lo}$ or $CD34^+Thy-1^+Lin^-Rh123^{lo}$ phenotype. It will be appreciated by those of skill in the art that the enrichment provided in any stem cell population will be dependent both on the selection-criteria used, as well as the purity achieved by the given selection techniques. Further, the LTCIC or CAFC frequencies obtained will vary depending on the assay conditions such as the stromal cells and cytokines used, although the enrichment in stem cell activity over that present in whole bone marrow will be comparable.

Stem cells may be isolated from any known human source of stem cells, including bone marrow, both adult and fetal, mobilized peripheral blood (MPB) and umbilical cord blood. Initially, bone marrow cells may be obtained from a source of bone marrow, including ilium (e.g. from the hip bone via the iliac crest), tibia, femora, spine, or other bone cavities. Other sources of stem cells include embryonic yolk sac, fetal liver, and fetal spleen.

For isolation of bone marrow, an appropriate solution may be used to flush the bone, including saline solution, conveniently supplemented with fetal calf serum (PCS) or other naturally occurring factors, in conjunction with an acceptable buffer at low concentration, generally from about 5-25 mM. Convenient buffers include HEPES, phosphate buffers and lactate buffers. Otherwise bone marrow may be aspirated from the bone in accordance with conventional techniques well known to those skilled in the art.

Methods for mobilizing stem cells into the peripheral blood are known in the art and generally involve treatment with chemotherapeutic drugs, e.g. cytoxan, cyclophosphamide, VP-16, and cytokines such as GM-CSF, G-CSF, or IL-3, or combinations thereof. Typically, apheresis for total white cells begins when the total white cell count reaches 500-2000 cells/µl and the platelet count reaches 50,000/µl. Daily leukapheris samples may be monitored for the presence of $CD34^+$ and/or $Thy-1^+$ cells to determine the peak of stem cell mobilization and, hence, the optimal time for harvesting peripheral blood stem cells.

Various techniques may be employed to separate the cells by initially removing cells of dedicated lineage ("lineage-committed" cells) Monoclonal antibodies are particularly useful for identifying markers associated with particular cell lineages and/or stages of differentiation. The antibodies may be attached to a solid support to allow for crude separation. The separation techniques employed should maximize the viability of the fraction to be collected.

The use of separation techniques include those based on differences in physical (density gradient centrifugation and counter-flow centrifugal elutriation), cell surface (lectin and antibody affinity), and vital staining properties. (mitochondria-binding dye rhodamine 123 and DNA-binding dye Hoechst 33342). Procedures for separation may include magnetic separation, using antibody-coated magnetic beads, affinity chromatography, cytotoxic agents joined to a monoclonal antibody or used in conjunction with a monoclonal antibody, including complement and cytotoxins, and "panning" with antibody attached to a solid matrix or any other convenient technique. Techniques providing accurate separation include flow cytometry which can have varying degrees of sophistication, e.g., a plurality of color channels, low angle and obtuse light scattering detecting channels, impedance channels, etc.

A large proportion of the differentiated cells may be removed by initially using a relatively crude separation, where major cell population lineages of the hematopoietic system, such as lymphocytic and myelomonocytic, are removed, as well as lymphocytic populations, such as megakaryocytic, mast cells, eosinophils and basophils. Usually, at least about 70 to 90 percent of the hematopoietic cells will be removed.

Concomitantly or subsequent to a gross separation providing for positive selection, e.g. using the CD34 marker, a negative selection may be carried out, where antibodies to lineage-specific markers present on dedicated cells are employed. For the most part, these markers include $CD2^-$, $CD3^-$, $CD7^-$, $CD8^-$, $CD10^-$, $CD14^-$, $CD15^-$, $CD16^-$, $CD19^-$, $CD20^-$, $CD33^-$, $CD38^-$, $CD71^-$, $HLA-DR^-$, and glycophorin A; preferably including at least $CD2^-$, $CD14^-$, $CD15^-$, $CD16^-$, $CD19^-$ and glycophorin A; and normally including at least $CD14^-$ and $CD15^-$. As used herein, $Lin^-$ refers to a cell population lacking at least one lineage specific marker. The hematopoietic cell composition substantially depleted of dedicated cells may be further separated using selection for $Thy-1^+$ and/or $Rho123^{lo}$, whereby a highly enriched stem cell population is achieved.

The purified stem cells have low side scatter and low to medium forward scatter profiles by FACS analysis. Cytospin preparations show the enriched stem cells to have a size between )mature lymphoid cells and mature granulocytes. Cells may be selected based on light-scatter properties as well as their expression of various cell surface antigens.

Preferably, cells are initially separated by a coarse separation, followed by a fine separation, with positive selection of a marker associated with stem cells and negative selection for markers associated with lineage committed cells. Compositions highly enriched in stem cells may be achieved in this manner. The desired stem cells are exemplified by a population with the $CD34^+Thy-1^+Lin^-$ phenotype, and are characterized by being able to be maintained in culture for extended periods of time, being capable of selection and transfer to secondary and higher order cultures, and being capable of differentiating into the various lymphocytic and myelomonocytic lineages, particularly B- and T-lymphocytes, monocytes, macrophages, neutrophils, erythrocytes and the like.

The stem cells may be grown in culture in an appropriate nutrient medium, including conditioned medium, a co-culture with an appropriate stromal cell line, or a medium comprising a-combination of growth factors sufficient to maintain the growth of hematopoietic cells. For conditioned media or co-cultures, various stromal cell lines may be used. Since human stromal cell lines are not required, other stromal cell lines may be employed, including rodentiae, particularly murine. Suitable murine stromal cell lines include-AC3 and AC6, which are described in Whitlock et al. (1987) Cell 48:1009-1021. Preferably, the stromal cell line used is a passage of AC6, AC6.21 (otherwise referred to as SyS1).

The compositions comprising stem cells can be tested for the ability to produce myeloid cells and lymphoid cells in appropriate stromal cell co-cultures. The stromal cells may come from various sources, including human, porcine or murine, by selection for the ability to maintain stem cells, and the like. Preferably, the stromal cells are AC3 or AC6, most preferably AC6.21, and the ability to produce-B lymphocytes and myeloid cells is determined in cultures supplied with LIF and IL-6. The stem cells also give rise to B-cells, T-cells and myelomonocytic cells in the in vivo assays described below.

To demonstrate differentiation to T-cells, fetal thymus is isolated and cultured from 4-7 days at about 25° C., so as to substantially deplete the lymphoid population. The cells to be tested for T-cell activity are then microinjected into the thymus tissue, where the HLA of the population which is injected is mismatched with the HLA of the thymus cells. The thymus tissue may then be transplanted into a scid/scid mouse as described in U.S. Pat. No. 5,147,784, herein specifically incorporated by reference, particularly transplanting under the kidney capsule. After 6 weeks, the thymus tissue is harvested and analyzed for donor-derived $CD4^+$ and/or $CD8^+$ T-cells by flow cytometry.

Further demonstration of the long-term repopulating ability of the stem cell populations useful in the invention may be accomplished by the detection of continued myeloid and B-lymphoid cell production in the SCID-hu bone model (Kyoizumi et al. (1992) Blood 79:1704). To analyze this, one may isolate human fetal bone and transfer a longitudinally sliced portion of this bone into the mammary fat pad of a scid/scid animal. The bone cavity is diminished in endogenous cells by whole body irradiation of the mouse host prior to injection of the test donor population. The HLA of the population which is injected is mismatched with the HLA of the recipient bone cells. Stem cells from human hematopoietic sources sustain B lymphopoiesis and myelopbiesis in the SCID-hu bone model.

For RBCs, one may use conventional techniques to identify burst forming unit-erythroid (BFU-E) units, for example methylcellulose culture, demonstrating that the cells are capable of developing into the erythroid lineage (Metcalf (1977) In: Recent Results in Cancer Research 61. Springer-Verlag, Berlin, pp. 1-227).

Effect of Thrombopoietin on Stem Cells

The human mpl transcript in highly purified bone marrow and mobilized peripheral blood $CD34^+Thy-1^+Lin^-$ stem cells was demonstrated by RT-PCR (Example 3). However, it was not know if the receptor is expressed on the cell surface or if a receptor ligand would have any effect on the cells.

The present study was initiated to determine whether TPO has any effect on primitive human hematopoietic stem cells ("HSC"), and if so, to define its range of activities. Initially, human TPO was cloned and sequenced based on the published sequence as described in Example 1.

Single $CD34^+Thy-1^{+Lin-}$ cells from adult bone marrow (ABM) were cultured individually in Terasaki wells on the murine stromal cell monolayer, SyS1, with TPO alone or in combination with cytokines IL-3, KL, IL-6, or LIF (Example 4). The growth of each cell was tracked by image acquisition, as described in Example 4. FIGS. 1A-1E show the maximum proliferation achieved over a 4 week period by each $CD34^+Thy-1^+Lin^-$ cell plated under various cytokine conditions from a representative ABM tissue. TPO alone supported a plating efficiency of 74% and an average cell production of 454 cells per cell. Plating efficiency is defined as the number of cells that divided one or more times/number of cells plated. When IL-3 was added, cell production was enhanced approximately 4-fold. This level of proliferation was similar to that achieved in the presence of combined IL-3, IL-6, LIF and KL. The results show that TPO acts directly on human $CD34^+Thy-1^+Lin^-$ cells to induce cycling of primitive noncommitted human hematopoietic progenitors (e.g., expressing CD34 but not lineage antigens), and that co-stimulation with IL-3 increases total cell production.

Approximately 50% of single $CD34^+Thy-1^+Lin^-$ cells grown in the presence of TPO displayed MK differentiation, as measured by size and CD41b antigen expression (Example 4). CD41b antigen expression is characteristic of cells committed to the MK lineage. These results demonstrate that TPO supports stem cell differentiation into MK lineage.

To quantitatively demonstrate that TPO was stimulating single stem cells to produce multiple MK progenitors prior to maturation, the number of CFU-MK present in populations of day 0 ABM $CD34^+Thy-1^+Lin^-$ cells were compared to the number obtained from wells of proliferating blast cells that grew from a single $CD34^+Thy-1^+Lin^-$ cell in the presence of TPO. In one representative experiment, day 0 $CD34^+Thy-1^+Lin^-$ cells produced 0.0026 CFU-MK per cell, compared to blast cell populations expanded from a single $CD34^+Thy-1^+Lin^-$ cell, which produced an average of 8.3 CFU-MK per original cell (range 1-18) in the presence of TPO and IL-3. This 10 represents an amplification in MK progenitor production during culture of 3,200-fold, and indicates that TPO can act on single human stem cells and permit commitment to the MK lineage, MK progenitor expansion, and MK maturation in culture.

In addition to promoting MK proliferation and differentiation, it has now been found that TPO acts on primitive HSC to promote expansion without differentiation into the MK lineage. This finding is surprising in light of the report that only the MK lineage is defective in mpl-deficient transgenic mice (Guerney et al. (1994) Science 265:1445). Approximately 50% of the single $CD34^+Thy-1^+Lin^-$ cells from ABM that grew in the presence of TPO did not display MK differentiation. A small proportion (lot of cells that grew) developed directly into large granular cells with macrophage characteristics. The remaining 40% of cells that grew formed tightly apposed clusters of blast cells (cobblestone areas) which did not differentiate to large refractile MK or large granular macrophage cells over a four week period. The addition of IL-3 to TPO increased the frequency of cells exhibiting a non-megakaryocytic blast cell expansion pattern from 40% to approximately 80% of single cells that grew, and increased the proliferation of single cells approximately 4-fold such that some wells reached the maximum capacity of the Terasaki well (approximately 10,000 cells).

To determine whether other cytokines alone, or in combination with TPO could support proliferation of primitive $CD34^+$ cells, cytokines with known activities on early hematopoietic cells were tested. Although $CD34^+$ cells were detected in cell populations expanded using IL-6+LIF+IL-3+KL, the highest percentages of $CD34^+$ cells were always found in wells which contained TPO (Table 1). A typical TPO-expanded blast population of approximately 1,000 cells, of which 2% are CD34 positive, represents an approximate 20-fold expansion of $CD34^+$ (Table 1).

A stromal support layer (SyS1) was used in the long-term culture assays herein described because previous observations showed that single or small numbers of HSC cultured under stroma-free conditions displayed more rapid differentiation and lower total cell production than those cultured on a stromal layer. SyS1 culture supernatants alone cannot substitute for the stromal cells for support of hematopoietic progenitors. In addition, single HSC plated on SyS1 without exogenous human cytokine addition show an extremely low growth frequency. The above findings made with single HSC grown on a stromal layer were substantiated by showing that in bulk cultures grown in the absence of stroma, purified recombinant TPO alone can activate quiescent HSC.

PKH26 is a fluorescent dye which labels cell membranes and reduces in intensity with each cell division. The effect of TPO on PKH26 fluorescence relative to CD34 expression was analyzed in stromal-free bulk cultures. For these experiments, an enriched quiescent ($CD34^+Lin^-Rh123^{lo}$) stem cell population was tested. PKH26 dye marking of cell membranes was used to obtain quantitation of cell divisions in conjunction with expression of the CD34 antigen to determine the effects of various cytokine combinations on stem cell proliferation and differentiation. TPO alone was able to stimulate these quiescent HSC to begin cycling within 3 days (FIG. 2C), and still retain high levels of CD34 expression after 6 days of culture (FIG. 2D). TPO alone caused greater activation than KL alone at 3 (FIG. 2E) and 6 days (FIG. 2F). When TPO and KL were combined, they acted synergistically to increase cell cycling by day 6 (FIG. 2L). IL-3 plus TPO produced much more cell proliferation than TPO alone, but caused more differentiation than TPO alone or TPO+KL (e.g., loss of CD34 expression) (FIGS. 2I and 2J).

Therapeutic Use of Thrombopoietin

The present invention is based on the discovery that mpl ligand, thrombopoietin, has unique and unexpected effects on human stem cells. As established by the evidence provided herein, exposure of human long-term repopulating stem cells to TPO results in cell expansion with minimal differentiation. TPO also causes expansion of human stem cells with subsequent differentiation to the MK lineage, as well as non-MK cells. Further, TPO is shown to activate quiescent human stem cells into cycle more quickly than other known cytokines. Additionally, TPO is herein shown to promote the survival of human stem cells in in vitro culture.

The subset of primitive human hematopoietic cells shown herein to respond to TPO are long-term repopulating or pluripotent stem cells, characterized by the ability to give rise to cells which retain the capability of self-renewal, and to proliferate and differentiate into cells of all hematopoietic lineages.

Use of TPO for Expansion of Long-Term Repopulating Cell Populations. The ability of TPO to induce extensive proliferation of a primitive human stem cell subpopulation without loss of the pluripotent capacity has important clinical implications for restoration of hematopoietic capability in subjects in which hematopoietic capability is lost or threatened. Accordingly, the invention features the use of TPO for in vitro expansion of a human long-term repopulating cell population. This is particularly useful for re-establishing hematopoietic capability in patients in which native hematopoietic capability has been partially, substantially, or completely compromised. Stem cells from any tissue are removed from a human subject, expanded in vitro by exposure to TPO, and the expanded cells are returned to the patient. If necessary, the process may be repeated to ensure substantial repopulation of the stem cells. The expanded stem cell population returned to the subject retain pluripotent characteristics, e.g., self-renewal and ability to generate cells of all hematopoietic lineages. By combination of various cytokines the expanded cell population will include progenitor cells and more mature cells of the various hematopoietic lineages (e.g., megakaryocytes, neutrophils) in addition to stem cells to provide a cell population that will provide both short-term and long-term repopulation potential.

Stems cells are preferably isolated from bone marrow or mobilized peripheral blood, and more preferentially from bone marrow. Expansion procedures may be conducted either with or without stromal cells. Stromal cells may be freshly isolated from bone marrow or from cloned stromal cell lines. Such lines may be human, murine, or porcine; preferably, the cell line is AC6.21, as described in the Examples below.

For clinical applications, it is preferred to culture the stem cells in the absence of stromal cells. During expansion, TPO may be present only during the initial course of the stem cell growth and expansion, usually at least 24 hours, more usually at least about 48 hours to 4 days, or more preferably is maintained during the course of the expansion. During cell expansion, TPO is present in a concentration range of 10-200 ng/ml; more-preferably, TPO is present in a concentration range of about 10-100 ng/ml. In addition, TPO may be combined with the use of other growth factor and cytokines, such as IL-3. During stem cell expansion, TPO is present in a concentration range of between about 1 ng/ml to about 200 ng/ml, preferably in the range of between about 50 ng/ml and 100 ng/ml, most preferably about 50 ng/ml. When cell expansion is conducted in the presence of TPO and IL-3, IL-3 is present in a concentration range of between about 1 ng/ml to about 100 ng/ml, preferably in the range of between about 5 ng/ml and 25 ng/ml, most preferably about 10 ng/ml. Additional regulatory factors may be present, for example, Stl (50-100 ng/ml), LIF (50 ng/ml), IL-6 (2-100 ng/ml), MIP-1α (2-100 ng/ml), Flk2/Flt3 (2-100 ng/ml), G-CSF (2-20 ng/ml), GM-CSF (2-20 ng/ml), IL-1 (2-100 ng/ml), and IL-11 (2-100 ng/ml). Various in vitro and in vivo tests known to the art may be employed to ensure that the pluripotent capability of the stem cells has been maintained.

Use of Thrombopoietin in Gene Therapy. TPO has been shown herein to stimulate a quiescent human long-term repopulating stem cell population to begin actively dividing without differentiation, e.g., culturing long-term repopulating stem cells in the presence of TPO results in the generation of cells which retain the capability of self-renewal and ability to give rise to cells of all hematopoietic lineages. This discovery is particularly important for transduction of human stem cells with exogenous genes because retroviral vectors require target cells to be cycling for stable integration of the retroviral DNA. The ability to modify a human pluripotent cell population should provide long-term repopulation of an individual with the modified cells and their progeny, which will express the desired gene product. By contrast, gene transfer into more mature hematopoietic cells, such as T cells, at best, provides only transient therapeutic benefit.

Thus, the use of TPO for transduction of stem cells satisfies the current world-wide effort to find effective methods of genetically modifying stem cells. For reviews of genetic modification of stem cells see Brenner (1993) J. Hematother. 2:7-17; Miller (1992) Nature 357:455-460; and Nienhuis (1991) Cancer 67:2700-2704.

While retroviral vectors may be used to genetically modify a population of human long-term repopulating stem cells, other methods may be used, such as liposome-mediated gene transfer or adeno-associated viral vectors. Retroviral vectors have been the primary vehicle due to the generally high rate of gene transfer obtained in experiments with cell lines, and the ability to obtain stable integration of the genetic material, which ensures that the progeny of the modified cell will contain the transferred genetic material.

Retroviral vectors and their use in the transfer and expression of foreign genes are reviewed in Gilboa (1988) Adv. Exp. Med. Biol. 241:29;.Luskey et al. (1990) Ann. N.Y. Acad. Sci. 612:398; and Smith (1992) J. Hematother. 1:155-166.

Hematopoietic stem cells are removed from a human patient, and a population of long-term repopulating stem cells isolated. These cells may be optionally expanded prior to or after modification by transduction with a vector carrying the desired gene. The modified cells are then restored to the human patient for expression of the foreign gene. The patient may be treated to partially, substantially, or completely ablate the native hematopoietic capability prior to restoration of the modified stem cells. Preferably, after completion of the treatment of the host, the modified stem cells may then be restored to the host to provide for expression of the foreign gene. The methods of stem cell removal, host ablation and stem cell repopulation are known in the art. If necessary, the process may be repeated to ensure substantial repopulation of the modified stem cells.

During optional expansion, TPO alone or combined with other growth factors may be present only during the initial course of the stem cell growth and expansion, usually at least 24 hours, more usually at least about 48 hours to 4 days, or may be maintained during the course of the expansion. Example 8 below describes a protocol for stem cell transduction in the presence of TPO. For use in clinical settings, it is preferable to transduce the stem cells without prior or subsequent expansion.

Transduction may be accomplished by the direct co-culture of stem cells with producer cells, e.g. by the method of Bregni et al. (1992) Blood 80:1418-1422. For clinical applications, however, transduction by culturing the stem cells with viral supernatant alone or with purified viral preparations, in the absence of stromal cells, is preferred. Transductions may be performed by culturing the stem cells with the virus for from about four hours to six days. Preferably, transduction is carried out for three days, with the media replaced daily with media containing fresh retrovirus. Alternatively, the stem cells may be cultured in the presence of virus for several hours, e.g., four hours, daily for three to four days, with fresh media replacing the virus-containing media each day. Polycations, such as protamine sulfate, polybrene and the like, will generally be included to promote binding. Protamine sulfate and polybrene are typically used in the range of 4 μg/ml.

Other cytokines may also be added, including, e.g., IL-3, IL-6, LIF, steel factor (Stl) GM-CSF, G-CSF, MIP-1α, and Flk2/Flt3, preferably including Stl. The factors employed may be naturally occurring or synthetic, e.g., prepared recombinantly, and preferably human. The amount of the factors will generally be in the range of about 1 ng/ml to 200 ng/ml. Generally, for TPO, the concentration will be in the range of about 1 ng/ml to 200 ng/ml, more usually 5 ng/ml to 100 ng/ml, and optimally about 10 ng/ml to 50 ng/ml; for Stl, the concentration range will be in the range of 10 ng/ml to 200 ng/ml, and more usually 50 ng/ml to 100 ng/ml; for LIF, the concentration will be in the range of about 1 ng/ml to 100 ng/ml, more usually 10 ng/ml to 80 ng/ml, and optimally about 50 ng/ml; for IL-3, the concentration will be in the range of about 5 ng/ml to 100 ng/ml, more usually 5 ng/ml to 50 ng/ml; for IL-6, the concentration will be in the range of about 5 ng/ml to 50 ng/ml, more usually 5 ng/ml to 20 ng/m, and for GM-CSF, the concentration will generally be 5 ng/ml to 50 ng/ml, more usually 5 ng/ml to 20 ng/ml.

To ensure that the stem cells have been successfully modified, PCR may be used to amplify vector specific sequences in the transduced stem cells or their progeny. In addition, the cells may be grown under various conditions to ensure that they are capable of maturation to all of the hematopoietic lineages while maintaining the capability, as appropriate, of the introduced DNA. Various in vitro and in vivo tests described above may be employed to ensure that the pluripotent capability of the stem cells has been maintained.

Gene Therapy Applications. Gene transfer into stem cells may be used to treat a variety of neoplastic, infectious or genetic diseases. For example, one may introduce genes that confer resistance to chemotherapeutic agents, thereby protecting the progeny hematopoietic cells, allowing higher doses of chemotherapy and thereby improving the therapeutic benefit of treatment. For instance, the mdr1 gene may be introduced into stem cells to provide increased resistance to a wide variety of drugs including taxol, which are exported by the mdr1 gene product, in combination with the administration of chemotherapeutics such as taxol, e.g. for breast cancer treatment. Similarly, genes that provide increased resistance to alkylating agents, such as melphalan, may be introduced into stem cells in conjunction with high dose chemotherapy.

For viral infections that primarily affect hematolymphoid cells, stem cells may be modified-to endow the progeny with resistance to the infectious agent. In the case of human immunodeficiency virus (HIV), for example, specific antisense or ribozyme sequences may be introduced that interfere with viral infection or replication in the target cells. Alternatively, the introduced gene products may serve as "decoys" by binding essential viral proteins, thereby interfering with the normal viral life cycle and inhibiting replication.

Alternatively, stem cells may be modified to produce a product to correct a genetic deficiency, or where the host has acquired a genetic deficiency through a subsequent disease. Genes that may correct a genetic deficiency include adenosine deaminase for the treatment of ADA severe combined immunodeficiency; glucocerebrosidase for the treatment of Gaucherh's disease; β-globin for the treatment of sickle cell anemia; and Factor VIII or Factor IX for the treatment of hemophilia; tumor antigen-specific T-cell receptors for immunotherapy of cancer, and cytokines for treatment of cancer and cytokine-related disorders.

Expression of the transferred gene can be controlled in a variety of ways depending on the purpose of gene transfer and the desired effect. Thus, the introduced gene may be put under the control of a promoter that will cause the gene to be expressed constitutively, only under specific physiologic conditions, or in particular cell types. Examples of promoters that may be used to cause expression of the introduced sequence in specific cell types include Granzyme A and Granzyme B for expression in T-cells and NK cells, the CD34 promoter for expression in stem and progenitor cells, the CD8 promoter for expression in cytotoxic T-cells, and the CD11b promoter for expression in myeloid cells. Inducible promoters may be used for gene expression under certain physiologic conditions. The therapeutic benefit may be further increased by targeting the gene product to the appropriate cellular location, for example, the nucleus, by attaching the appropriate localizing sequences. In addition, by appropriate use of inducible promoters, expression of various protein products can be achieved in response to particular stimuli such as chemicals, chemo-attractants, particular ligands, and the like.

EXAMPLE 1

Cloning and Expression of Thrombopoietin

TPO cDNA was cloned using the polymerase chain reaction from human fetal liver cDNA (Clontech, Palo Alto, Calif.), using oligonucleotides based on the published sequence (de Sauvage et al. (1994) supra.), and expressed in COS cells. TPO-containing COS supernatants were shown to be active in stimulating the proliferation of mpl-expressing BaF3 cells (activity was 3×105 U/ml, where 50 U/ml=50% maximum activity), which were constructed by stable transfection of BaF3 cells with a human mpl expression construct as previously described (de Sauvage et al. (1994) supra). Mock transfected COS supernatant (COS control) was harvested from COS cells transfected with an empty expression vector, and had no effect on the proliferation of BaF3 cells.

EXAMPLE 2

Cell Selection

Enrichment of progenitor cells from human adult bone marrow and mobilized peripheral blood. Human adult bone marrow (ABM) CD34+ cells were enriched as follows. Briefly, fresh 20 ml bone marrow aspirates from normal volunteer donors were obtained from Stanford University Medical Center (Palo Alto, Calif.) or Scripps Research Institute (La Jolla, Calif.). Mononuclear cells (density<1.077) were isolated from a Ficoll (Pharmacia, Milwaukee, Wis.) density gradient in cell separation medium [RPMI 1640 (JRH Biosciences, Lenexa, Kans.), 10% fetal bovine serum (FBS) (Gemini Bioproducts, Calabasas, Calif.), 50 U/ml penicillin and 50 µg/ml streptomycin (JRH Biosciences)]. CD34 positive selection was performed by the method of Sutherland et. al (1992) Exp. Hematol. 20:590). The glycoprotease from *Pasteurella haemolytica* used for the bead release step in this procedure has been shown not to effect subsequent ex vivo expansion of progenitors (Marsh et al. (1992) Leukemia 6:929).

Stem cells were mobilized into the peripheral blood (MPB) of multiple myeloma patients and collected by leukapheresis as described by Murray et al. (1995) supra. MPB CD34$^+$ cells were enriched from leukapheresis products by using a procedure involving elutriation, phenylmethylester lysis of granulocytes, and ammonium chloride lysis of red blood cells and CD34 positive selection as described by Sutherland et al. (1992) supra.

Antibodies. TuK3 (anti-CD34) directly conjugated to sulpharhodamine (SR) and GM201 (anti-human Thy-1) directly conjugated to phycoerythrin (PE) were used to purify primitive progenitors by flow cytometry. FLOPC 21 mouse IgG3 (Sigma, St. Louis, Mo.) and purified mouse IgG1 (Becton Dickinson, Mountain View, Calif.) were conjugated to SR and PE, respectively, and used as controls for CD34 and Thy-1 staining. Fluorescein isothiocyanate (FITC)-conjugated lineage antibodies were used to exclude lineage positive cells from selection [Leu-5b (anti-CD2), Leu-M3 (anti-CD14), Leu-M1 (anti-CD15), Leu-11a (anti-CD16), Leu-12 (anti-CD19)], FTC-conjugated mouse IgG1 and IgG2a, PE and FITC-conjugated HPCA2 (anti-CD34) and mouhse IgG1 were purchased from Becton Dickinson. FITC-conjugated antibody D2.10 (anti-glycophorin) was purchased from AMAC (Westbrook, Me.). FITC-conjugated mouse IgM was purchased from Sigma (St. Louis Mo.). Human gamma globulin (Gamimune), was purchased from Miles Inc. (Elkhart, Ind.).

Fluorescent labeling and flow cytometry. CD34$^+$ enriched hematopoietic cells were adjusted to a concentration of 2×10$^6$/ml in staining medium [RPMI 1640 without phenol red, 2% FBS, and 10 mM HEPES (Sigma, St. Louis, Mo.)] and labeled using the following procedure performed on ice.

Heat inactivated human gamma globulin (Gamimune) was added to the cell suspension at a concentration of 1 mg/ml to block Fc receptor binding sites. Cells were incubated with anti-CD34-SR (10 µg/ml), anti-Thy-1-PE (10 µg/ml), and a mixture of FITC-conjugated antibodies directed against a panel of lineage markers. The mixture included anti-CD2, anti-CD14, anti-CD15, anti-CD16, anti-CD19, and anti-glycophorin A. Irrelevant mouse IgG3-SR (10 µg/ml) and IgG1-PE (10 µg/ml) antibodies were used as controls for CD34 and Thy-1 staining. FITC-conjugated mouse IgG1, IgG2a, and IgM were used as controls for the lineage panel. Incubation time for staining was 20 minutes followed by a three ml wash with staining medium.

Following antibody staining, cells were resuspended at a concentration of $10^6$ cells/ml in staining medium containing 1 µg/ml propidium iodide (PI) (Molecular Probes Inc., Eugene Ore.). Fluorescently stained cells were analyzed and sorted on a FACStar Plus cell sorter (Becton Dickinson). Dead cells (PI positive) and lineage positive cells (stained with an intensity above the isotype matched control antibody staining) were excluded from the sort gate. The CD34$^+$Thy-1$^+$ and, in some cases, CD34$^+$Thy-1$^-$, fractions were sorted from the live, lineage-negative cells (CD34$^+$Thy-1$^+$Lin$^-$ or CD34$^+$Thy-1$^-$Lin$^-$).

CD34$^+$ selected ABM cells were loaded with rhodamine 123 dye (Rh123) (Molecular Probes, Eugene, Oreg.), and allowed to efflux at 37° C. for 20 min, according to the method of Spangrude et al. (1988) Science 241:58-62, herein specifically incorporated by reference. The cells were then chilled to 4° C. and reacted with anti-CD34-SR and the same lineage marker antibodies as described above except conjugated to PE. Cells with a CD34$^+$Lin$^-$Rh123$^{lo}$ phenotype were purified by flow cytometry.

EXAMPLE 3

PCR Detection of MPL in Bone Marrow and Mobilized Peripheral Blood Samples

Cell lysates were prepared from total human bone marrow cells and bone marrow or mobilized peripheral blood cells of the phenotypes CD34$^+$Thy-1$^+$Lin$^-$ (Thy$^+$) and CD34$^+$Thy-1$^-$Lin$^-$ (Thy$^-$), isolated as described in Example 2. RNA was prepared using RNA STAT60 (Tel-Test, Inc.) according to the manufacturer's instructions. CDNA was made from each of the RNA samples using BRL Superscript RT following the manufacturer's instructions. One-fifth of the cDNA was then used for the first degenerate PCR reaction. The degenerate PCR primers designed to amplify sequences related to the Epo receptor and mpl receptor of the class I hemopoietin receptor family are as follows:

```
Sense primer HEpM1-5 (SEQ ID NO:1):
5'-GCTATTGCGGCCGCGAATTCGGARGAYYTIINITGYTTYTGG-3'

Antisense primer HEpM2-3: (SEQ ID NO:2)
5'-GCTATTCTCGAGATCGATSWCCAITCRCTCCAIIINCC-3'

Antisense primer HEpM3-3: (SEQ ID NO:3)
5'-GCTATTCTCGAGATCGATSWCCAINIRCTCCAIIINCC-3'
```

(R=A,G; Y=C,T, I=inosine; S=G,C; W=A,T). Restriction sites were added at the 5' end of each primer. One set of the reaction was performed with HEpM1-5 and HEpM2-3, and another reaction with was performed with HEpM1-5 and HEpM3-3. In each case, a smear was obtained.

The two PCR products (2 µl of each) were mixed for the second PCR reaction. The second PCR was carried out using specific primers to mpl. The following two sets of primers were used:

```
Set A:

sense primer mpl-5'(317-336) (SEQ ID NO:4):
5'-CGCTGCACCTCTGGGTGAAG-3' antisense primer mpl-3'(568-588) (SEQ ID NO:5):
5'-AGCAGGGCAGCAGGTTTCTGT-3'

Set B:

sense primer mpl-5'(317-336) (SEQ ID NO:4) and
antisense primer mpl-3-HI(754-774) (SEQ ID NO:6):
5'-GCTGCGCAGCTGCAGCCAGTA-3'
```

Results. In total bone marrow samples, mpl was detected with mpl-5'/mpl-3' primers alone. In sorted bone marrow samples, mpl was detected in both Thy$^+$ and Thy$^-$ samples using both sets of primers. mpl was detected using both sets of primers in peripheral blood samples (Thy$^+$ and Thy$^-$).

EXAMPLE 4

Effect of TPO on Single Cell Cultures of Stem Cells

Terasaki plates used for single cell deposition were pre-seeded with a murine stromal cell line (AC6.21, also referred to as SyS1) described previously (Baum et al. (1992) Proc. Natl. Acad. Sci. USA 89:2804; DiGiusto et al. (1994) Blood 84:421; Murray et al. (1995) supra), at approximately 50 cells per well in 20 µl of stromal cell culture medium [RPMI 1640, 5% FBS, $10^{-5}$ M 2-mercaptoethanol (2-ME) (Sigma), 4 mM glutamine (JRH Biosciences), 50 U/ml penicillin, and 50 µg/ml streptomycin]. Stromal cells were allowed to form a confluent monolayer by culturing for 4-7 days. At confluence monolayers were irradiated (1,000 rads from a cesium source) to prevent overgrowth. Immediately prior to seeding of hematopoietic cells, 10 µl of medium was removed and replaced with 10 µl stem cell culture medium (SCCM) [IMDM (JRH Biosciences), 5% pooled human plasma (HP), 7.5×$10^{-3}$ M α-TG (Aldrich Chemical Co. Milwaukee, Wis.), $10^{-5}$ M 2-ME, 100 mM Na pyruvate (JRH Biosciences), 4 mM glutamine, 50 U/ml penicillin, 50 µg/ml streptomycin]. The culture medium was chosen for maintenance of MK integrity which included human plasma (HP) and α-TG. SCCM was supplemented with combinations of cytokines as indicated. Cytokines included recombinant human (rh)IL-3 (10 ng/ml) (Genzyme, Cambridge, Mass.), rhIL-6 (10 ng/ml) (Sandoz, Basel, Switzerland), rhKL (25 ng/ml) and rhLIF (10 ng/ml) (Tago/Biosource, Camarillo, Calif.) and 10% supernatant collected from COS cells transfected with a TPO expression vector or 50 ng/ml rhTPO (R & D Systems, Minneapolis, Minn.,). Supernatant collected from COS cells transfected with an empty expression vector was used as a control for TPO-containing COS supernatant.

Single CD34$^+$Thy-1$^+$Lin$^-$ adult bone marrow (ABM) cells were cultured in the presence of 10% control COS supernatant (controls), 10% COS supernatant from COS cells transfected with TPO, 10% TPO COS supernatant+10 ng/ml IL-3, 10% TPO COS supernatant +25 ng/ml KL, or in the presence of 10 ng/ml IL-3, IL-6, and LIF, and 25 ng/ml KL.

Imaging and cell number quantitation. Images of Terasaki well single cell cultures were digitized and stored twice weekly. Magnification was adjusted such that the entire well was visible in each image. An inverted Nikon Diaphot microscope and Hamamatsu C2400 Newvicon CCD camera were used for image acquisition. Image-1 image analysis software and Compaq 66-MHz 486 computer (digitizing hardware)

were used (Universal Imaging, Philadelphia, Pa.). A Panasonic LF-7010 rewritable optical disk drive was used for image storage.

Cell numbers were determined from the image series by direct counting (<100 cells); or by estimating the proportion of the well filled (>100 cells). Average cell number in confluent wells was determined by hemacytometer counting.

Phenotynic analysis of subconfluent and confluent culture wells. Analysis of CD34 expression on cultured cells by flow cytometry was carried out as follows. Briefly, single cells which grew to fill an entire Terasaki well with blast cells were individually analyzed for the percentage of primitive progenitors ($CD34^+$ cells). The contents of subconfluent Terasaki wells (30-90% filled with blast cells) were pooled for analysis. Hematopoietic cells were removed from the wells by gentle pipetting, resuspended in 100 µl staining medium, and stained with anti-CD34 (HPCA2)-PE. A pool made from a small aliquot from each of the wells was used for control staining with IgG1-PE. A well was considered to contain a $CD34^+$ population if greater than 1% of the cells showed a level of fluorescence above that of the isotype control.

MK Progenitor Fibrin Clot Assay. The serum-depleted fibrin clot assay for colony-forming unit-megakaryocyte (CFU-MK) has been described previously (Bruno et al. (1989) Blood 73:671; Briddell et al. (1989) Blood 74:145). This assay compared the number of CFU-MK present in populations of day 0 ABM $CD34^+Thy-1^+Lin^-$ cells to the number obtained from wells of proliferating blast cells that grew from a single $CD34^+Thy-1^+Lin^-$ cell in the presence of TPO. Freshly sorted cells were plated at $10^4$ cells/ml, or blast populations harvested from Terasaki wells after 3 weeks of culture were plated in the fibrin clot assay in the presence of IL-3 at 10 ng/ml (Sandoz, Basel, Switzerland), GM-CSF at 2 ng/ml, and KL at 100 ng/ml (R&D Systems, Minneapolis, Minn.). Fibrin clots were fixed and analyzed for $CD41b^+$ colonies at 12 days.

Figure 1B:
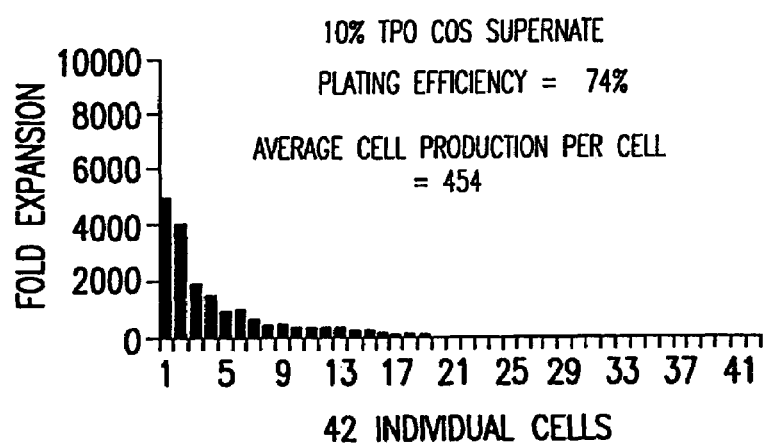
FIG. 1B is a graph showing the proliferative capacity of $CD34^+Thy-1^+Lin^-$ cells purified from ABM and cultured individually in the presence of 10% supernatant from COS cells transfected with TPO. Data was determined as described in the legend to FIG. 1A.
Figure 1C:
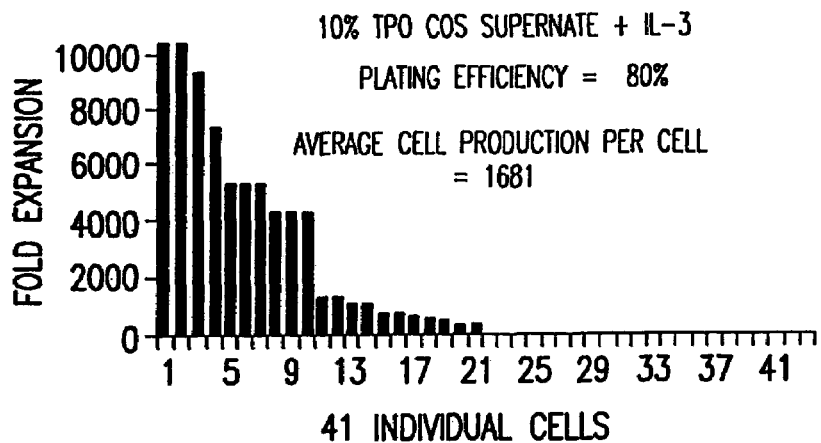
FIG. 1C is a graph showing the proliferative capacity of $CD34^+Thy-1^+Lin^-$ cells purified from ABM and cultured individually in the presence of 10% TPO COS supernatant and 10 ng/ml interleukin 3 (IL-3). Data was determined as described in the legend to FIG. 1A.
Figure 1D:
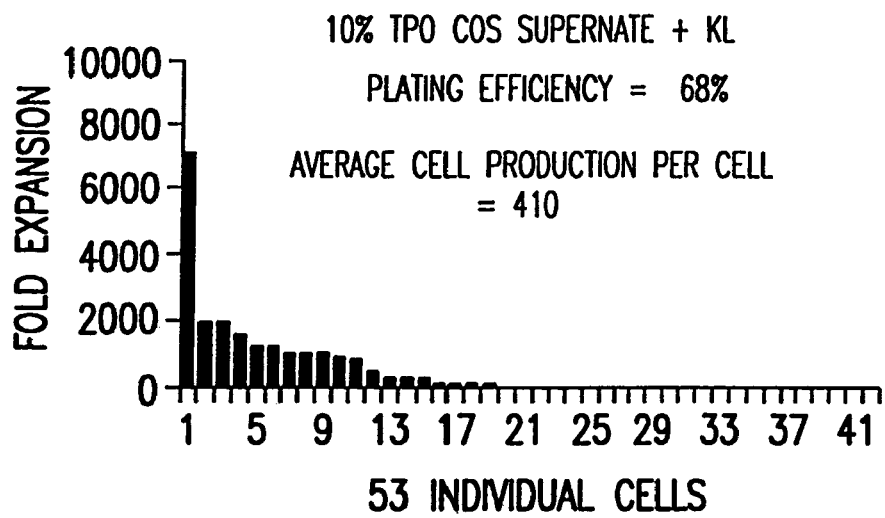
FIG. 1D is a graph showing the proliferative capacity of $CD34^+Thy-1^+Lin^-$ cells purified from ABM and cultured individually in the presence of 10% TPO COS supernatant and 25 ng/ml c-kit ligand (KL). Data was determined as described in the legend to FIG. 1A.
Figure 1E:
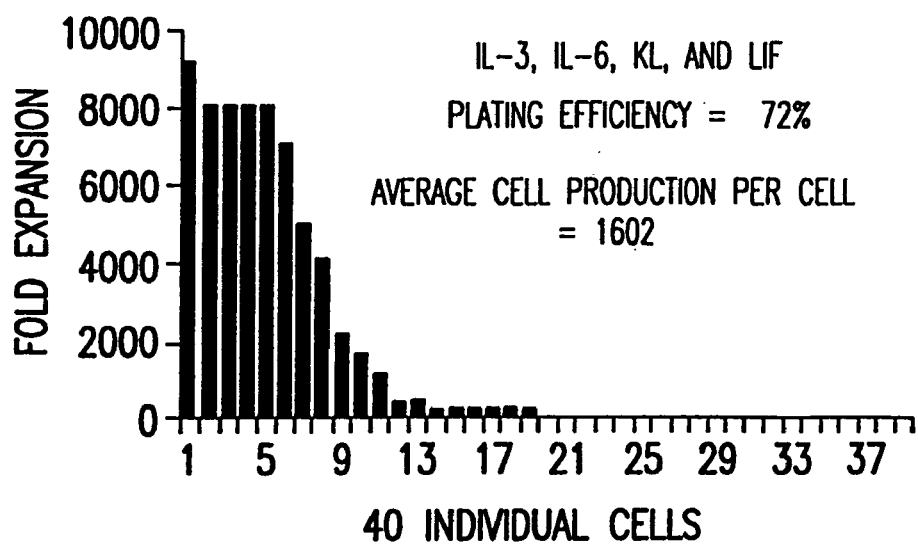
FIG. 1E is a graph showing the proliferative capacity of $CD34^+Thy-1+Lin^-$ cells purified from ABM and cultured individually in the presence of 10 ng/ml IL-3, 10 ng/ml IL-6, 10 ng/ml leukemia inhibitory factor (LIF), and 25 ng/ml KL. Data was determined as described in the legend to FIG. 1A.

Results. The effects of TPO on single cell cultures grown in the presence or absence of other cytokines are shown in FIGS. 1A-1E. The plating efficiency (number of single cells that divided one or more times/number of cells plated) and the average cell proliferation achieved by all single cells plated, are also shown. Control COS supernatant alone did not stimulate proliferation of $CD34^+Thy-1^+Lin^-$ cells (FIG. 1A). TPO-containing COS supernatant supported a plating efficiency of 74% and an average cell production of 454 cells per cell (FIG. 1B). When 25 ng/ml KL was used in combination with TPO COS supernatant, no augmentation of growth over TPO alone was observed (FIG. 1D). TPO plus 10 ng/ml of IL-3 enhanced cell production over TPO alone approximately 4-fold (1,681 cells/input cell) (FIG. 1C). This level of proliferation was similar to that achieved with a combination of four cytokines. (IL-3, IL-6, LIF, and KL) (FIG. 1E). Results were similar when purified rhTPO was used (data not shown).

TPO Expansion of Blast Cells. To determine whether TPO alone, or in combination with other cytokines could support proliferation of primitive $CD34^+$ cells, single $CD34^+/Thy-1^+Lin^-$ cells were cultured in the presence of 5% TPO COS supernatant, TPO+IL-3, TPO+KL, IL-3+IL-6+KL+LIF, and IL-3+IL-6+Kl+LIF+TPO. Cells were harvested from culture wells at 4-6 weeks, and either analyzed individually or pooled with other wells grown under like conditions. Cell populations were fluorescently stained with anti-CD34 antibody and analyzed by flow cytometry as described above. These populations contained from 0.5-4.4% $CD34^+$ cells, average 2.8% for TPO alone compared to 1% for TPO+IL-3, 1.2% for TPO+KL, 0.5% for IL-3+IL-6+LIF+KL, and 2.1% for TPO+LIF+KL+IL-3+IL-6. Thus, in these cultures TPO increased the expansion of $CD34^+$ cells, compared to other Cytokines tested, without differentiation into the MK lineage. Blast cell outgrowths did not express CD41b by immunocytochemical staining.

TPO Effect on Growth Morphology of $CD34^+Thy-1^+Lin^-$ Cells. The effect of TPO on MK differentiation was determined by size, phenotype, and expression of CD41b antigen expression by the methods described above.

Approximately 50% of single $CD34^+Thy-1^+Lin^-$ cells from ABM which grew in the presence of TPO displayed MK differentiation, as determined by a growth pattern of initial expansion and dispersal of 10-200 refractile blast cells over the stromal cell layer, followed by differentiation into large 25-50 nm refractile cells. This process occurred over a 2-3 week period from initial plating. Wells containing cells with this growth morphology were harvested and analyzed for CD41b expression by immunocytochemical staining. Essentially all hematopoietic cells in these populations stained positively for CD41b. This included the large cells as well as those that were still quite small in size.

To quantitatively demonstrate that TPO was stimulating single stem cells to produce multiple MK progenitors prior to maturation, the number of CFU-MK present in populations of day 0 ABM $CD34^+Thy-1^+Lin^-$ cells were compared to the number obtained from wells of proliferating blast cells that grew from a single $CD34^+Thy-1^+Lin^-$ cell in the presence of TPO. Freshly sorted cells, or blast populations harvested from Terasaki wells after three weeks of culture were placed in the fibrin clot assay. Colonies containing MKs were enumerated after immunofluorescent staining of the fibrin clot cultures with anti-CD41b antibody. In one representative experiment, 5,000 day 0 $CD34^+Thy-1^+Lin^-$ cells produced 13 MK colonies or 0.0026 colonies per cell. Seven individual blast cell populations, each arising from one cell, produced an average of 8.3 CFR-MK per-cell (range 1-18) in the presence of TPO and IL-3. This represents a 3,200-fold amplification of MK progenitor production during culture. These findings indicate that TPO can act on single human stem cells and permit commitment to the MK lineage, MK progenitor expansion, and MK maturation in culture.

EXAMPLE 5

Effects of TPO on Cobblestone Area Forming Cells (CAFC)

Limiting dilution (LD) cultures were established by-plating $CD34^+Thy-1^+Lin^-$ cells in Whitlock/Witte medium (50% IMDM (JRH Biosciences), 50%- RPMI 1640, 10% FCS, $4 \times 10^{-5}$ M 2-mercaptoethanol, 10 µm HEPES, 100 U/ml penicillin, 100 mg/ml streptomycin, and 4 mM glutamine) at limiting dilution (from 100-0.8 cells/well) on preformed SyS1 stromal monolayers, as described previously (Murray et al. (1995) supra). Four cytokine conditions were compared: (1) 5% control mock-transfected COS supernatant; (2) 5% TPO-containing COS supernatant; (3) 50 ng/ml LIF+10 ng/ml IL-6; and (4) 50 ng/ml LIF+10 ng/ml IL-6+5% TPO supernatant. In one experiment, purified TPO (R&D Systems) was used at 10 ng/ml. Cultures were fed at weekly intervals and scored at week 4 for cobblestone area formation. Wells containing cobblestone areas were analyzed for CD34 expression.

TPO Effect on Size and Frequency of Cobblestone Areas. LD cultures grown with medium alone or with 5% control COS supernatant showed almost no growth, whereas cultures grown with 5% TPO-containing COS supernatant showed increased cell growth, including growth of cobblestone areas.

LD cultures grown in the presence of LIF and IL-6, showed cobblestone area formation as observed previously (Murray et al. (1995) supra). However, when TPO was added to LIF and IL-6, the cobblestone areas appeared earlier, at higher frequency (Table 2), and grew to a much larger size by 4 weeks. When these wells were analyzed for CD34 expression, 69% contained CD34+ cells compared to 38% of wells grown in LIF and IL-6 alone. Similar results were obtained with purified rhTPO. In agreement with the findings obtained with single cell culture, TPO increased the expansion of CD34+ cells from primitive progenitors cultured at limiting dilution (Table 3).

EXAMPLE 6

Expansion Effects of TPO $CD34^+$, $CD34^+Lin^-$ or $CD34^+Thy-1^+Lin^-$ ABM cells were cultured on SyS1 stromal cells in SCCM with the indicated cytokines and analyzed at days 7 and 11.

Expansion Effect of TPO on ABM $CD34^+$ selected cells. The purity of glycoprotease-selected $CD34^+$ cells ranged from 60-93%. TPO alone induced a 1.3-fold expansion of $CD34^+$ by day 11, at which time a mean of 52.8% MKs were observed (Table 4). Wright-Giemsa staining showed both small and large MKs, the latter with multilobulated nuclei, indicative of polyploidization. Immunocytochemistry confirmed that both small and large cells were positive for CD41b expression, showing commitment to the MK lineage. Although, IL-3 is known as an MK stimulatory factor, only 3% MKs were detectable at day 11 when $CD34^+$ cells were cultured in IL-3 alone. A combination of TPO, IL-3, and KL resulted in a 4.7-fold lower percentage of MKs at day 11, while the number of total cells increased 5.5-fold, producing a similar or slightly higher number of MKs at day 11. Results are shown in Table 5.

Expansion Effect of TPO on ABM $CD34^+Lin^-$ selected cells. $CD34^+Lin^-$ cells (depleted of $CD2^+$, CD15+, and $CD19^+$ cells) purified by FACS sorting had purities from 87% to 96%. In the presence of TPO alone, total cell expansion was greater than that observed with $CD34^+$ cells (Table 6). By day 11, there was a 10-fold greater total cell expansion in cells cultured with TPO+IL-3 compared to TPO alone, but the proportion of MKs was approximately 3.5-fold lower (Table 5). TPO+IL-3 generated a 2-fold higher number of total MKs by day 11, but the MKs were a minority of the population, the majority of cells appearing myeloid (Table 5). The addition of GM-CSF to TPO resulted in a 2.8-fold greater cell expansion by day 11, but the percentage of MKs remained slightly higher than with TPO+IL-3 (33.7% vs. 20.6%) (Table 5). A higher absolute number of MKs at day 11 could be produced by addition of either IL-3 or GM-CSF to TPO, but at the expense of the purity of the MK population.

Figure 3A:
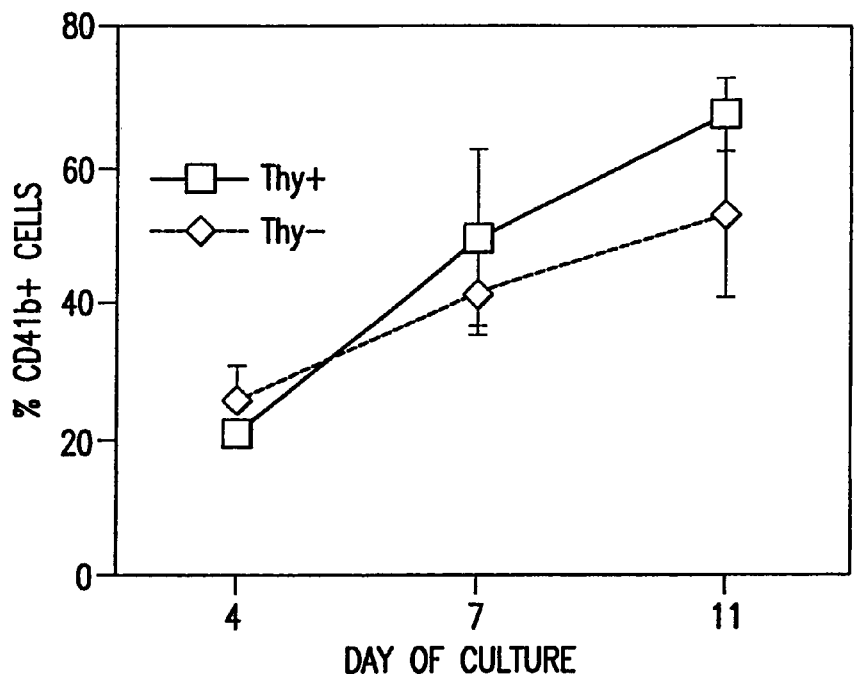
FIG. 3A is a graph showing the effect of TPO on the expansion of the $CD41b^+$ cell population of cultured $CD34^+Lin^-$ and $CD34^+Thy-1^+Lin^-$ cells.
Figure 3B:
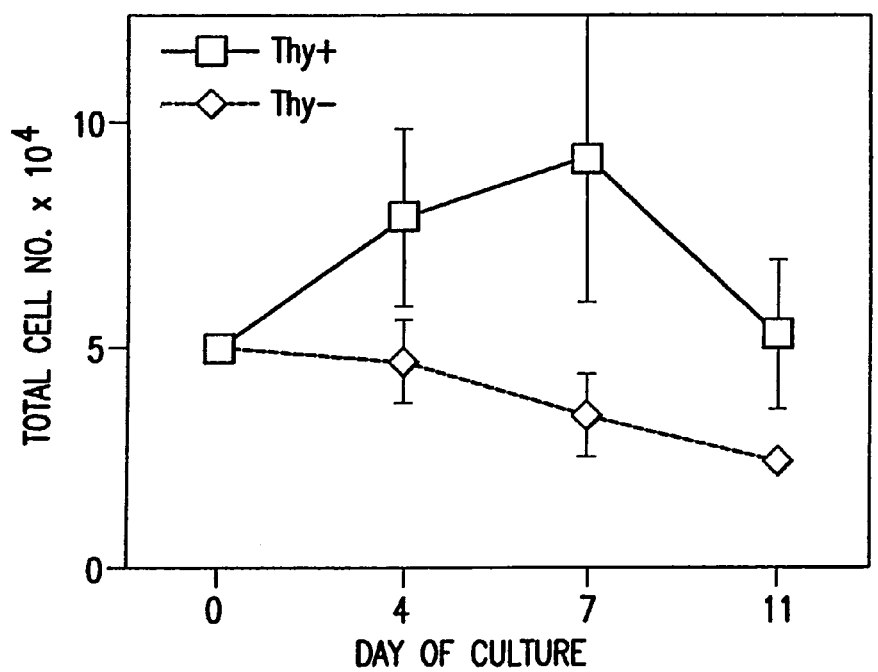
FIG. 3B is a graph showing the effect of TPO on total cells numbers of cultured $CD34^+Lin^-$ and $CD34^+Thy-1^+Lin^-$ cells.

Effect of TPO on ABM $CD34^+Thy-1^+Lin^-$. Using the original sort gates, purity of the $Thy-1^+$ cell subpopulations ranged from 77-90% (mean 84%) and of the $Thy-1^-$ cell subpopulations from 65-93% (mean 86%). There was significant cell expansion from the $Thy-1^+$ population and a high percentage of MKs were consistently observed by day 11 (61.9-77.6%), indicating that $CD34^+Thy-1^+Lin^-$ stem cells can mature into MKs under the stimulation of TPO alone. The differences in MK potential between the $Thy-1^+$ and $Thy-1^-$ cell subpopulations were not significant (FIGS. 3A & 3B). Table 6 summarizes the mean total cell expansion and MK production of each cell subpopulation at days 7 and 11 under these conditions.

EXAMPLE 7

TPO Stimulates Activation of Quiescent Stem Cells into Cycle

To determine if TPO could activate quiescent stem cells into cycle, the effect of TPO on primitive hematopoietic cells which could efflux Rh123, ($CD34^+Lin^-$ $Rh123^{lo}$) was tested. This cell population was labeled with the membrane dye PKH26, so that cell division could be observed by loss of PKH fluorescence. Labeling was performed per manufacturer's instructions (Zynaxis Cell Sciences Inc., Malvern, Pa.).

The $CD34^+Lin^-Rh123^{lo}$ cells labeled with PKH26 dye were cultured for up to 6 days as follows: approximately $10^4$ cells were seeded in SCCM without stroma at 100 µl/well in round bottom 96 well plates with either no added cytokines (negative control), or the cytokine indicated (FIGS. 2A-2L). Cells were cultured in the presence of TPO, KL, or IL-3 alone, TPO and KL, or TPO and IL-3, and then analyzed at day 3 and day 6. Cultures were harvested, stained with anti-CD34-FITC antibody, and analyzed by flow cytometry for CD34 expression versus PKH26 dye retention on days 3 and 6 of culture. To obtain a day 0 measurement, an aliquot of cells was taken following staining and incubated overnight at 37° C. to allow complete efflux of the Rh123 dye. Cells were then stained with anti-CD34-FITC and analyzed by flow cytometry. Cycling of cells was indicated by loss of PKH fluorescence, while differentiation was indicated by loss of CD34 expression.

Figure 2A:
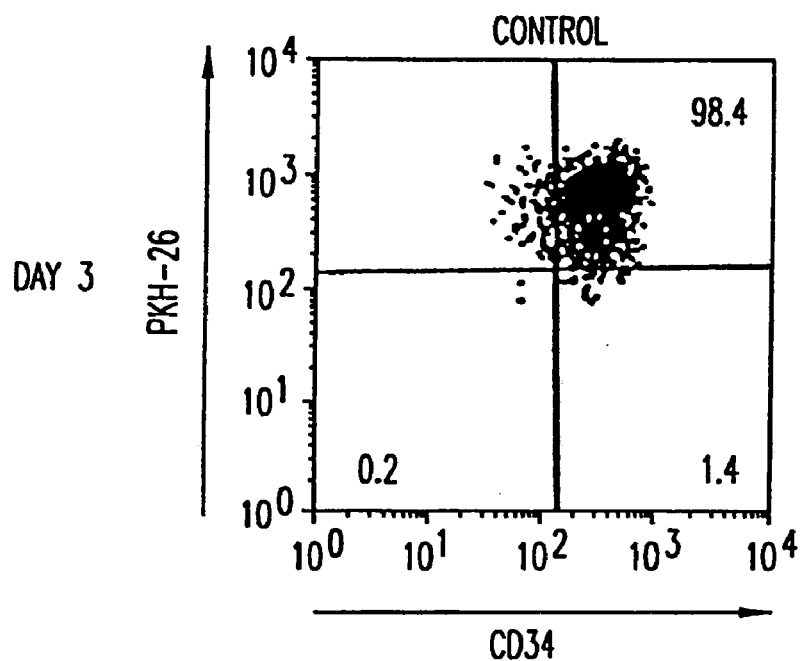
FIGS. 2A-2L are FACScan analysis of PKH26 and CD34 fluorescence in $CD34^+Lin^-Rh123^{lo}$ cells. ABM $CD34^+Lin^-Rh123^{lo}$ cells were labeled with PKH26 membrane dye and cultured for 3 or 6 days without (control) or with TPO, KL, IL-3, IL-3+TPO, or KL+TPO in suspension cultures in the absence of stroma. Following culture, the cells were reacted with anti-CD34-FITC antibody and PKH26 vs. CD34 fluorescence was analyzed on a FACScan analyzer. The percentages of CD34 and PKH26 positive or negative cells are shown in the quadrants. Quadrants were set based on day 0 (uncultured) cells, and on cells cultured in the absence of exogenous cytokines on day 3 and day 6. Day 3.
Figure 2B:
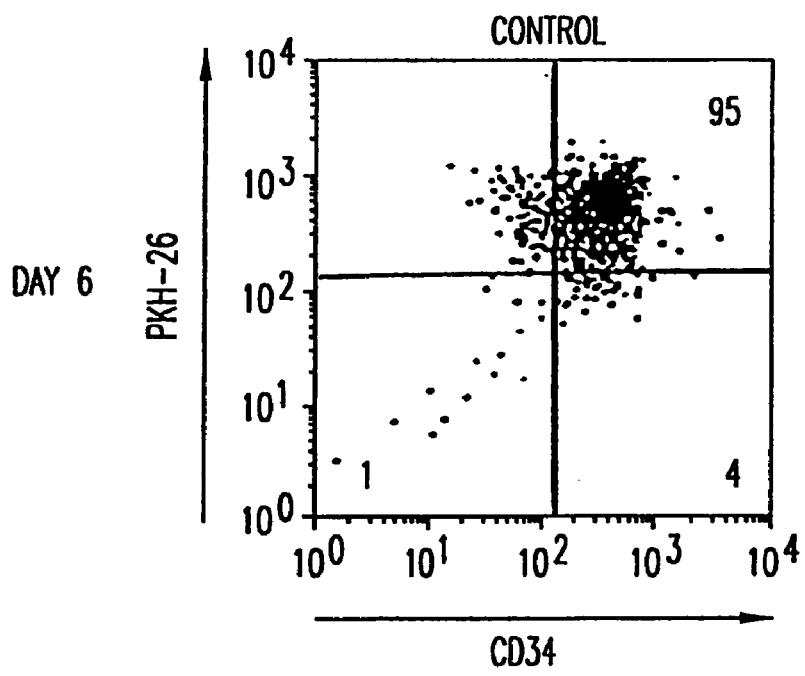
Figure 2C:
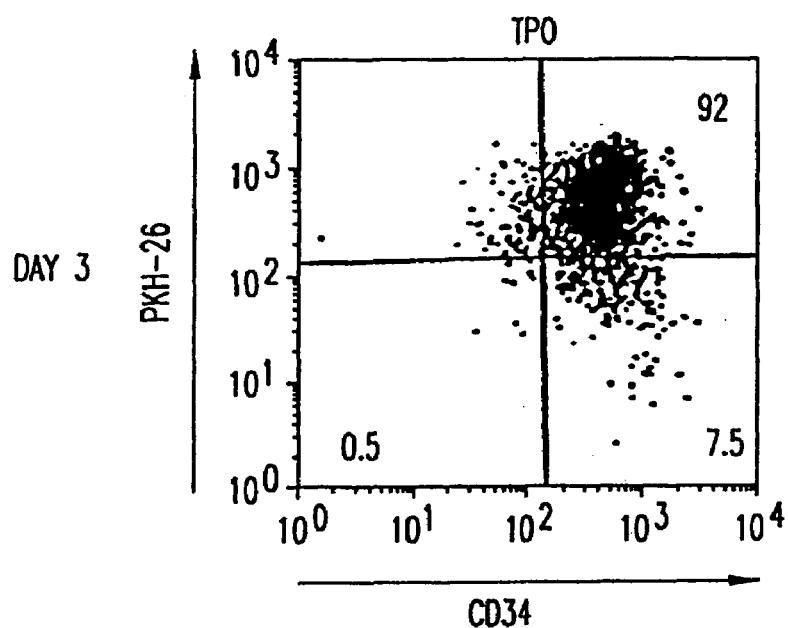
Figure 2D:
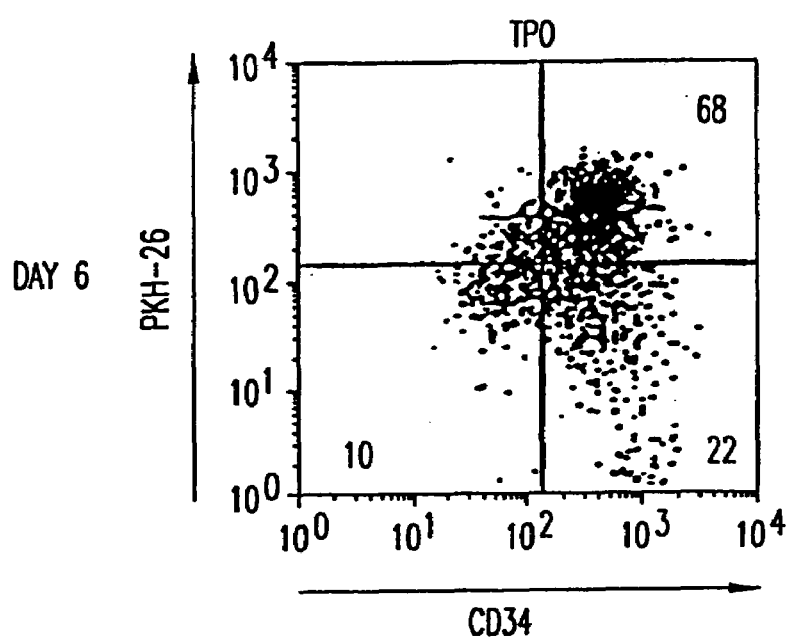
Figure 2E:
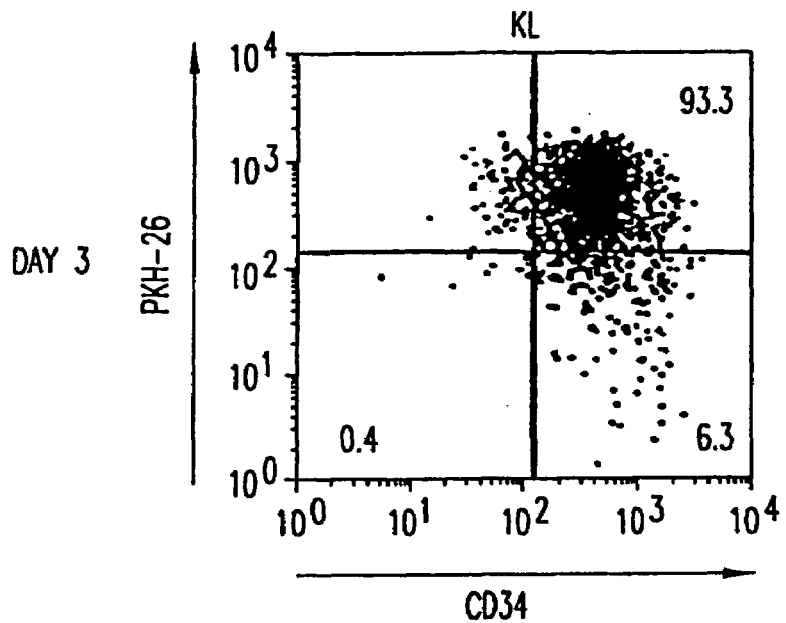
Figure 2F:
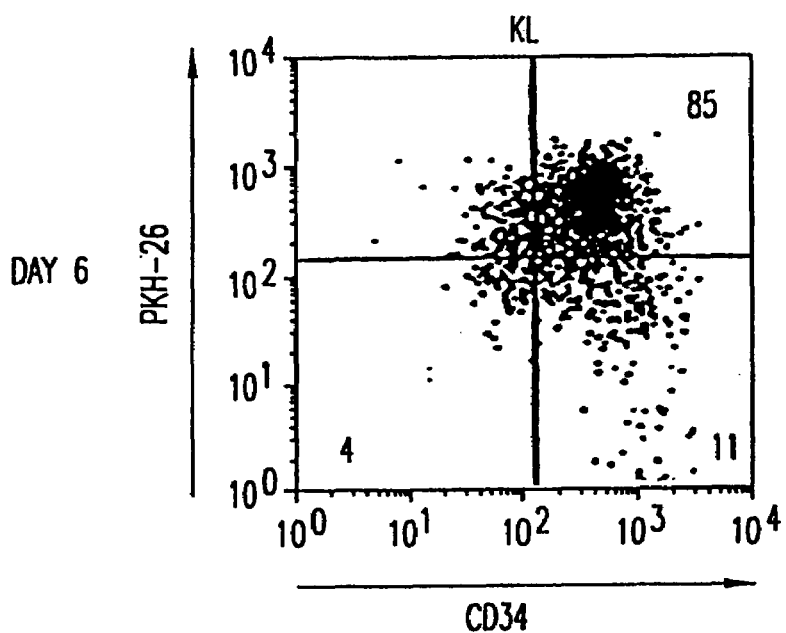
Figure 2G:
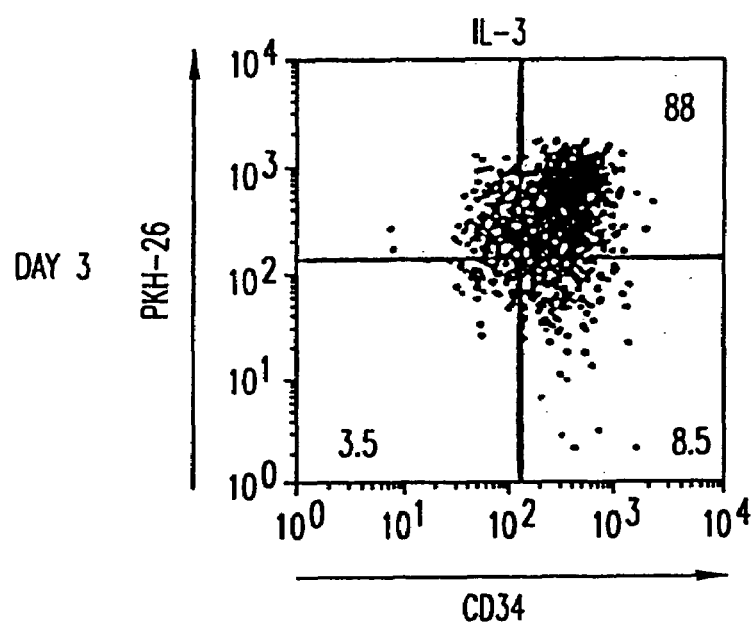
Figure 2H:
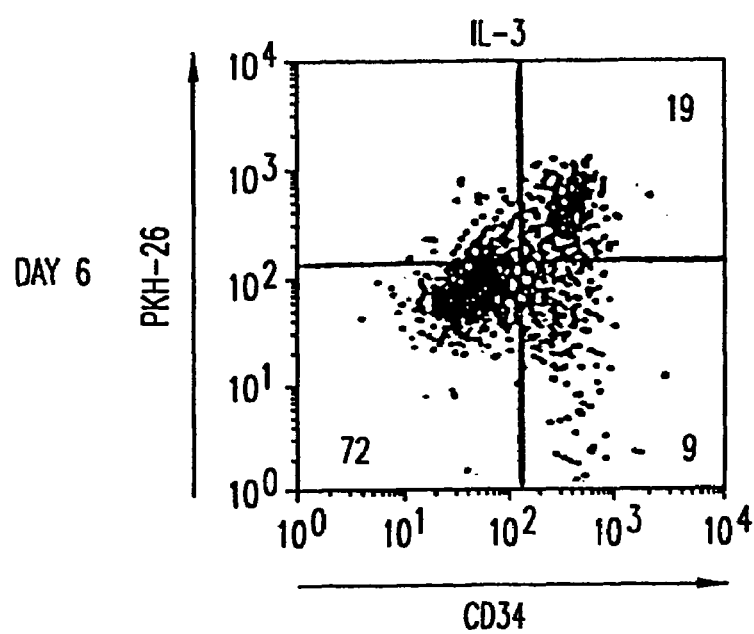
Figure 2I:
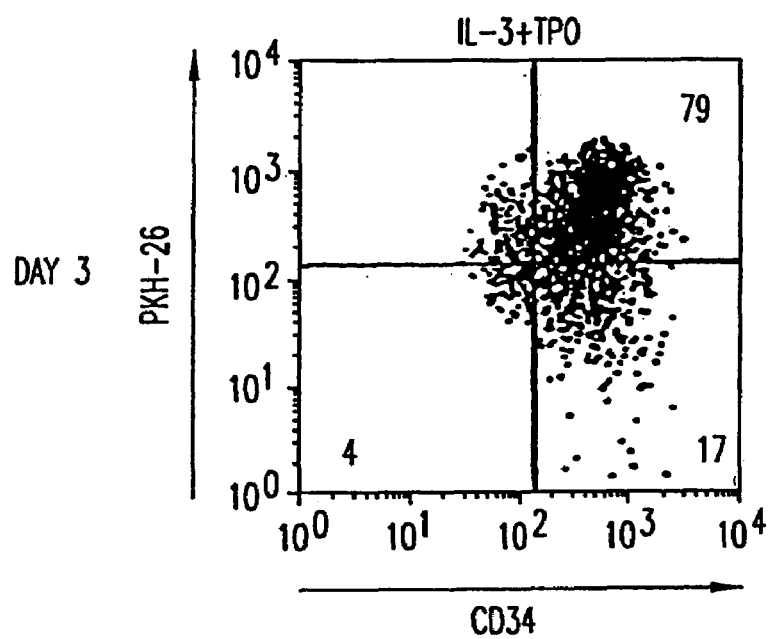
Figure 2J:
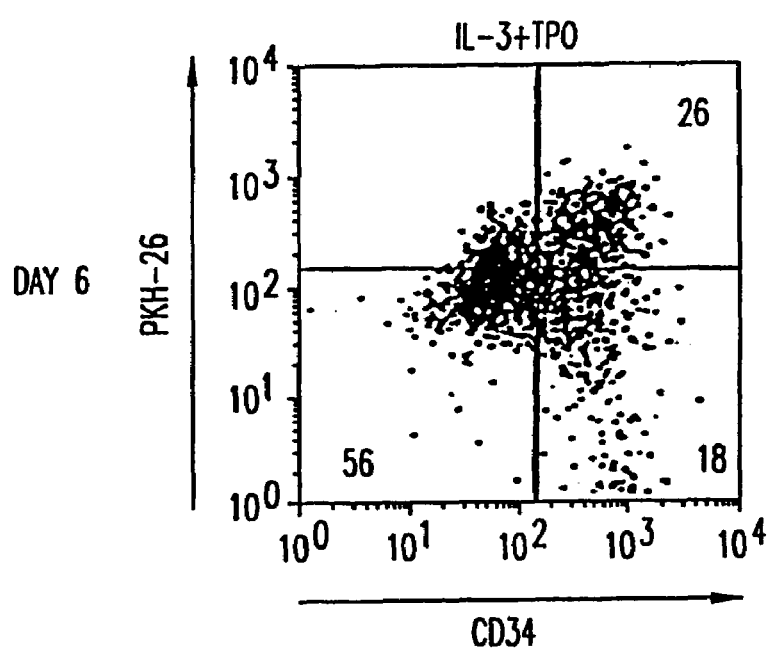
Figure 2K:
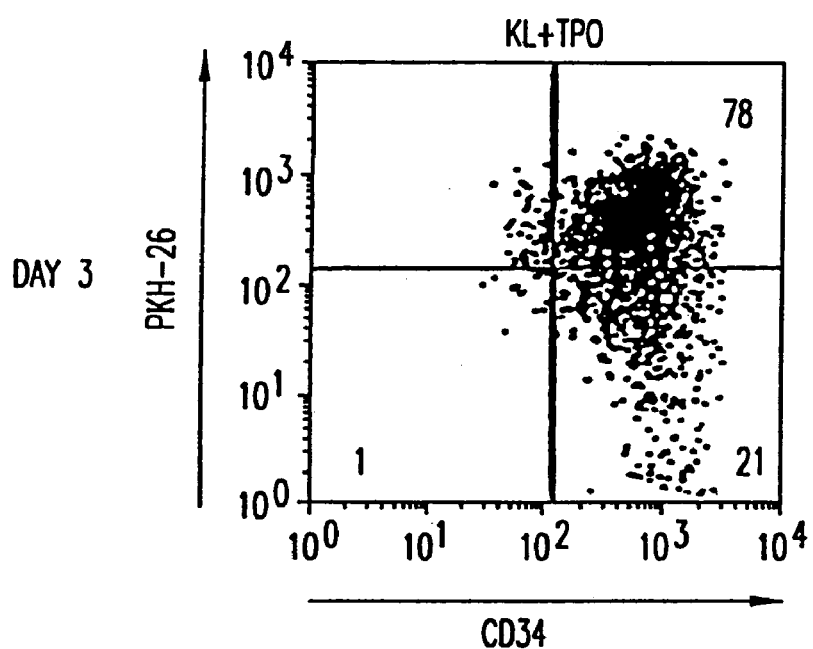
Figure 2L:
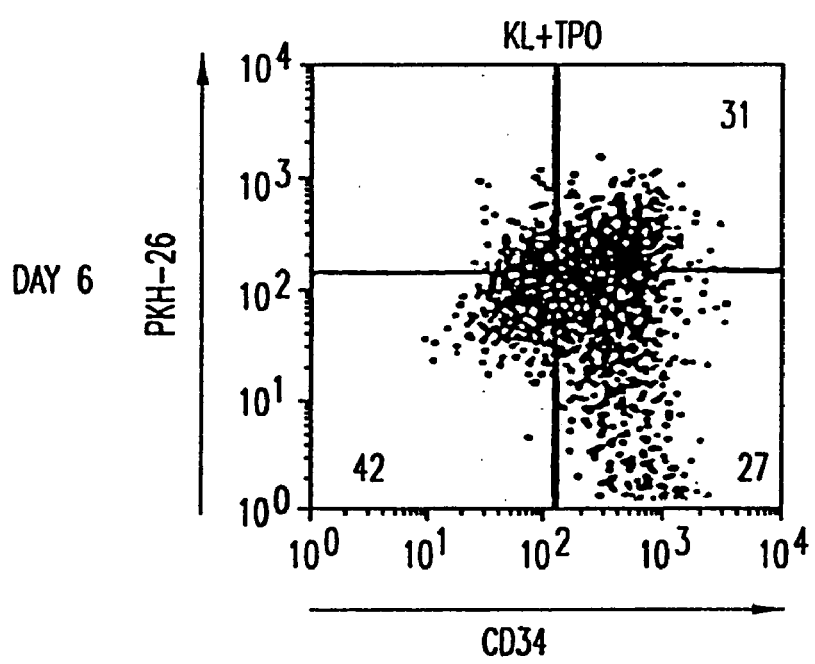

FIGS. 2A-2L show a representative summary of 3 experiments using purified rhTPO. Similar results were also obtained in two previous experiments using 10% TPO-containing COS supernatant. In serum-containing medium, in the absence of added cytokines, the cells remained in the upper right quadrant (there was no loss of PKH26 fluorescence or CD34 expression) showing that the cells remained quiescent (FIGS. 2A and 2B). By day 3 of culture with rhTPO, about 8% of $Rho123^{lo}$ cells had divided (FIG. 2C). By day 6, 32% of the cells were cycling, and ⅔ of these expressed CD34 (FIG. 2D). At day 3 the effect of TPO and KL was similar (FIG. 2E), but by day 6, higher percentages of CD34+ cells were retained in the presence of TPO (FIG. 2F and FIG. 2D). When TPO and KL were combined, activation of cells into cycle by day 3 was more than additive, and occurred without loss of CD34 expression (FIG. 2K). There was apparent synergy between KL and TPO by day 6 with 69% of the cells entering cycle, however, 62% of cycling cells had differentiated to CD34– cells (FIG. 2L). IL-3 alone stimulated the greatest degree of cycling by day 6, however, the vast majority of these cells had lost CD34 expression, indicating that IL-3 pushed differentiation at the expense of self-renewal (FIG. 2H). With the addition of TPO to IL-3, more dividing cells retained CD34 expression at days 3 and 6 than seen with IL-3 alone (FIG. 2J), although fewer dividing cells were $CD34^+$ as compared to cultures with both TPO and KL.

EXAMPLE 8

Effect of TPO on Transduction of Stem Cells $CD34^+Thy-1^+Lin^-$ stem cells are selected from mobilized peripheral blood or ABM as described above. Transduction experiments are conducted by methods known to the art in combination with the present disclosure. In addition to TPO (10-100 ng/ml purified recombinant TPO) the transduction medium may contain cytokines such as KL, IL-3, IL-6, etc.

The LN retroviral vector contains the bacterial neo gene as a selectable marker under the control of the Herpes Simplex Virus thymidine kinase (HSV-tk) promoter, with the therapeutic gene of interest inserted under the control of the Moloney murine leukemia virus long terminal repeat (MMLV-LTR) (Miller & Rosman (1989) Biotechniques 7:980). The retroviral vector DNA is electroporated (Chu et al. (1987) Nucleic Acids Res. 15:1311) into the amphotropic PA317 packaging cells (Miller & Buttimore (1986) Mol. Cell. Biol. 6:2895) and the cells are selected in 600 mg/ml G418 (Gibco-BRL). Virus from resistant PA317 cells are used to inoculate GP-E86 cells (Markowitz et al. (1988) J. Virol. 62:1120) and G418-resistant cell populations are again established. Virus from GP-E86 cells are used to inoculate PA317 cells at high multiplicity of infection (>10) and individual G418-resistant PA317 cell clones are isolated. A single clone producing high titer viral supernatants (>1×10$^6$ G418-resistant CFU/ml as determined on NIH 3t3 cells) is selected. The producer cells test negative for replication competent retrovirus (RCR) in S+L− assays on PG-4 cells (Haapala et al. (1985) J. Virol. 53:827). Vector-producing cells are grown in DMEM with high glucose and 10% FCS. Supernatant is harvested 24 hr after a media change on confluent monolayers and stored at −70° C.

Viral supernatant is diluted 1:1 in 2× transduction medium (Whitlock/Witte medium plus cytokines and 4 ug/ml protamine sulfate) prewarmed to 37° C., and sorted cells are suspended in the diluted viral supernatant at about 5×10$^5$ cells/ml. The same procedure is followed in the absence of TPO (control). After 4 hrs, the medium is removed from the cells, and the cells resuspended in fresh medium (without virus) with or without TPO and/or additional cytokines, and the cells repipetted into the original well. The cultures are incubated for another 20 hrs. The process is repeated for three consecutive days with the cells incubated in the presence of virus for 4 hr each day. After 72 hrs, a viable cell count is performed. Transduction frequency is improved when the cells are transduced as described above but sample are centrifuged at 2800×g at 21° C. during the 4 hr incubation period.

To determine transduction frequency, 2.5-5×10$^3$ cells from each transduction are added to 5 ml of methylcellulose (Stem Cell Technologies) containing the following cytokines: KL, 10 ng/ml; GM-CSF, 25 ng/ml; G-CSF, 25 ng/ml; IL-3, 10 ng/ml; and rhEPO, 2 units/ml. 1.1 ml of the cell/cytokine methylcellulose mixture is plated onto four 3 cm gridded plates using a 5 ml syringe and 16.5 gauge needle, and the plates are placed in a 37° C. incubator for 2 weeks. After 14 days, single methylcellulose colonies are picked and suspended in 50 μl Lysing Buffer (75 mM KCl, 10 mM Tris-HCl, pH 9.25, 1.5 mM MgCl$_2$, 0.5% Tween-20, 0.5% NP40, 1 mg/ml proteinase K) and PCR used to amplify vector-specific sequences in the transduced cells. PCR products are visualized on ethidium bromide agarose gels.

Long term stromal cultures are used to evaluate gene markings of more primitive progenitor cells. Briefly, 10,000 cells from each transduction are cultured for 4 weeks on a pre-established monolayer of mouse stromal cells (AC6.21) in media supplemented with 20 ng/ml LIF and 20 ng/ml IL-6. Plates are fed weekly by demi-depletion and growth positive wells are analyzed by PCR for the presence of the transgene.

Results. Cells transduced in the presence of TPO will exhibit improved cell viability relative to cell transduced in the absence of TPO, hence resulting in higher numbers of transduced stem cells. Transduction frequencies are improved in the presence of IL-3 and KL, in addition to TPO, which promote cell viability, cell cycling and binding of amphotropic retrovirus to human hematopoietic stem cells.

TABLE 1

Single HSC per well culture: analysis of CD34$^+$ cells

| ABM | week analyzed | # wells | TPO % CD34$^+$ | TPO + IL-3 % CD34$^+$ | TPO + KL % CD34$^+$ | 3 + 6 + KL + LIF % CD34$^+$ | 3 + 6 + KL + LIF + TPO % CD34$^+$ |
|---|---|---|---|---|---|---|---|
| 1 | 4 | 1 | ND | 0 | ND | ND | ND |
|   | 4 | 1 | ND | 0 | ND | ND | ND |
|   | 5 | 1 | ND | 1.7 | ND | ND | ND |
|   | 5 | 1 | ND | 2.5 | ND | ND | ND |
|   | 6 | pool | 0.5 | ND | 1.2 | 1.0 | ND |
| 2 | 4 | pool | 3.5 | ND | ND | ND | ND |
| 3 | 4 | pool | 4.4 | ND | ND | 0 | 2.1 |
| AVE |   |   | 2.8 | 1.0 | 1.2 | 0.5 | 2.1 |

TABLE 2

Effect of TPO on CAFC frequency

| | Cytokines added | | | |
|---|---|---|---|---|
| ABM | 0 | TPO | LIF + IL-6 | LIF + IL-6 + TPO |
| 4* | 1/1389 | 1/82 | 1/44 | 1/19 |
| 5* | <1/10,000 | 1/745 | 1/228 | 1/33 |
| 6** | <1/10,000 | 1/3060 | 1/649 | 1/142 |

*TPO-containing COS supernatant
**10 ng/ml rhTPO

TABLE 3

Limiting dilution culture: analysis of CD34$^+$ cells

| ABM | TPO (% CD34$^+$) | LIF + IL-6 (% CD34) | LIF + IL-6 + TPO (% CD34) |
|---|---|---|---|
| 4 | 13.1 | 3.0 | 14.7 |
| 5 | 4.5 | 0 | 4.5 |
| 6 | 4.3 | 1.8 | 6.3 |

TABLE 4

Effect of TPO and IL-3 with or without KL on ABM CD34+ selected cells

| Addition | % CD41b+ cells | | | total cell no. ×10$^4$ | | |
|---|---|---|---|---|---|---|
| | day 4 | day 7 | day 11 | day 4 | day 7 | day 11 |
| 0 | 4.4 ± 0.8 | 4.6 ± 2.2 | ND | 7.8 ± 1.1 | 6.0 ± 1.6 | ND |
| IL-3 | 6.0 ± 1.4 | 7.2 ± 1.8 | 3.0 ± 0.2 | 12.5 ± 0.5 | 13.1 ± 1.9 | 15.6 ± 3.2 |
| TPO | 20.8 ± 0.0 | 42.4 ± 7.0 | 52.8 ± 2.8 | 11.2 ± 0.2 | 11.5 ± 0.4 | 13.2 ± 0.8 |
| TPO + IL-3 | 20.1 ± 5.3 | 25.0 ± 3.6 | 32.0 ± 22.2 | 18.8 | 11.0 | 32.9 |
| IL-3, TPO + KL | 6.7 ± 2.6 | 11.0 ± 1.0 | 11.3 ± 3.7 | 34.1 ± 17.6 | 34.8 ± 7.9 | 72.1 ± 4.3 |

TABLE 5

Effect of TPO with or without IL-3 or GM-CSF on CD34+Lin− cells

| ABM | Addition | % CD41b+ cells | | | total cell no. ×10$^4$ | | |
|---|---|---|---|---|---|---|---|
| | | day 4 | day 7 | day 11 | day 4 | day 7 | day 11 |
| 1 | TPO | 19.8 | 70.6 | 70.1 | 34.0 | 28.5 | 34.2 |
| | TPO + IL-3 | 14.8 | 14.0 | 15.2 | 67.0 | 95.3 | 276.4 |
| | TPO + GM-CSF | 16.0 | 30.7 | 34.0 | 25.0 | 52.3 | 104.6 |
| 2 | TPO | 39.7 | 43.7 | 61.4 | 20.6 | 28.0 | 74.2 |
| | TPO + IL-3 | 15.2 | 17.1 | 21.0 | 90.0 | 132.0 | 204.6 |
| | TPO + GM-CSF | 29.3 | 31.9 | 33.3 | 27.4 | 88.8 | 195.4 |
| 3 | TPO | 27.5 | 53.5 | 75.6 | 15.5 | 40.3 | 19.7 |
| | TPO + IL-3 | 22.0 | 31.2 | 25.6 | 23.5 | 131.6 | 355.8 |
| | TPO + IL-3 + GM-CSF | 16.5 | 23.7 | 16.3 | 68.6 | 164.6 | 117.7 |

TABLE 6

Comparison of ABM CD34+ Cell Subpopulations

| Population | Additions | Total cell no. ×10$^4$ | No. CD41b+ cells | % CD41b+ cells |
|---|---|---|---|---|
| Day 7 | | | | |
| CD34+ | TPO | 11.5 | 4.9 | 42.4 |
| | TPO + IL-3 | 11.0 | 2.8 | 25.0 |
| CD34+Lin− | TPO | 32.3 | 18.1 | 55.9 |
| | TPO + IL-3 | 120.0 | 25.0 | 20.8 |
| CD34+Thy+Lin− | TPO | 18.4 | 9.2 | 49.6 |
| | TPO + IL-3 | 14.5 | 7.1 | 48.8 |
| Day 11 | | | | |
| CD34+ | TPO | 13.2 | 7.0 | 52.8 |
| | TPO + IL-3 | 32.9 | 10.5 | 32.0 |
| CD34+Lin− | TPO | 42.7 | 29.5 | 69.0 |
| | TPO + IL-3 | 279.0 | 57.5 | 20.6 |
| CD34+Thy+Lin− | TPO | 10.5 | 7.1 | 67.5 |
| | TPO + IL-3 | 10.5 | 7.7 | 73.7 |

What is claimed is:

1. An in vitro method of expanding a population of hematopoietic stem cells, comprising exposing said hematopoietic stem cell to a mpl ligand, wherein said cell proliferates to form an expanded population of hematopoietic stem cells.

2. The method of claim 1, wherein said mpl ligand is thrombopoietin.

3. The method of claim 2, wherein said thrombopoietin is human thrombopoietin.

4. The method of claim 3, wherein said thrombopoietin is recombinant human thrombopoietin.

5. The method of claim 1, wherein said expanded cell population is characterized by the ability to undergo substantial self-renewal and ability to give rise to all hematopoietic cell lineages.

6. The method of claim 1, wherein said cells are human stem cells.

7. The method of claim 6, wherein said cell is $CD34^+$.

8. The method of claim 6, wherein said cell is $CD34^+Lin^-$.

9. The method of claim 6, wherein said cell is $CD34^+Thy^+Lin^-$.

10. The method of claim 6, wherein said cell is $CD34^+Lin^-Rho^{lo}$ or $CD34^+Thy^+Lin^-Rho^{lo}$.

11. The method of claim 4, wherein said recombinant human thrombopoietin is present in a concentration of about 1 ng/ml to about 100 ng/ml.

12. An in vitro method for activating a quiescent hematopoietic stem cell to divide, comprising exposing said quiescent stem cell to a mpl ligand, wherein said cell is activated to divide.

13. The method of claim 12, wherein said mpl ligand is thrombopoietin.

14. The method of claim 13, wherein said thrombopoietin is human thrombopoietin.

15. The method of claim 14, wherein said thrombopoietin is recombinant human thrombopoietin.

16. The method of claim 12, wherein said cell is a human stem cell.

17. The method of claim 16, wherein said cell is $CD34^+$.

18. The method of claim 16, wherein said cell is $CD34^+Lin^-$.

19. The method of claim 16, wherein said cell is $CD34^+Thy^+Lin^-$.

20. The method of claim 16, wherein said cell is $CD34^+Lin^-Rho^{lo}$ or $CD34^+Thy^+Lin^-Rho^{lo}$.

21. The method of claim 12, wherein cells formed from said activated cell are characterized by the capability of self-renewal and ability to give rise to all hematopoietic cell lineages.

22. The method of claim 15, wherein said recombinant human thrombopoietin is present in the concentration range of about 1 ng/ml to about 100 ng/ml.

* * * * *